United States Patent
Seal et al.

(10) Patent No.: US 12,090,249 B2
(45) Date of Patent: Sep. 17, 2024

(54) IMPLANT AND COATING TO REDUCE OSTEOLYSIS

(71) Applicants: University of Central Florida Research Foundation, Inc., Orlando, FL (US); Sanford Burnham Prebys Medical Discovery Institute, La Jolla, CA (US)

(72) Inventors: Sudipta Seal, Orlando, FL (US); Soumen Das, Orlando, FL (US); William Self, Oviedo, FL (US); Dwight Towler, La Jolla, CA (US)

(73) Assignees: University of Central Florida Research Foundation, Inc., Orlando, FL (US); Sanford Burnham Prebys Medical Discovery Institute, La Jolla, CA (US)

( * ) Notice: Subject to any disclaimer, the term of this patent is extended or adjusted under 35 U.S.C. 154(b) by 711 days.

(21) Appl. No.: 17/202,527

(22) Filed: Mar. 16, 2021

(65) Prior Publication Data
US 2021/0290822 A1 Sep. 23, 2021

Related U.S. Application Data

(62) Division of application No. 15/766,582, filed as application No. PCT/US2016/055683 on Oct. 6, 2016, now Pat. No. 11,007,303.
(Continued)

(51) Int. Cl.
*A61L 27/30* (2006.01)
*A61L 27/04* (2006.01)
(Continued)

(52) U.S. Cl.
CPC ............. *A61L 27/306* (2013.01); *A61L 27/04* (2013.01); *A61L 27/10* (2013.01); *A61L 27/14* (2013.01);
(Continued)

(58) Field of Classification Search
CPC ........ A61L 27/306; A61L 27/04; A61L 27/10; A61L 27/14; A61L 27/54;
(Continued)

(56) References Cited

U.S. PATENT DOCUMENTS

| 6,713,671 B1 | 3/2004 | Wang et al. |
| 7,504,356 B1 | 3/2009 | Self et al. |

(Continued)

FOREIGN PATENT DOCUMENTS

| WO | 2014134286 | 9/2014 |
| WO | 2017062573 | 4/2017 |

OTHER PUBLICATIONS

Yang et al, "Electrodeposition of cerium oxide films and composites", Surface & Coatings Technology, 206 (2011), 1-7 (Year: 2011).*

(Continued)

*Primary Examiner* — Xiuyu Tai
(74) *Attorney, Agent, or Firm* — Timothy H. Van Dyke; Wolter, Van Dyke, Davis, PLLC

(57) ABSTRACT

An implant is provided comprising a substrate having one or more nanoceria coatings coated at least partially thereon, wherein the one or more nanoceria coatings comprise surface cerium having a 3+/4+ oxidation state ratio such that the one or more nanoceria coatings exhibit catalase mimetic activity, superoxide dismutase mimetic activity, or both. Methods are provided for forming a nanoceria coating. The coating has nanoceria having a surface cerium 3+/4+ oxidation state ratio such that such that the coating exhibits (Continued)

catalase mimetic activity, superoxide dismutase mimetic activity, or both. Also disclosed is a method of reducing degradation of an implant by placing nanoceria in proximity to a bone-implant interface.

6 Claims, 12 Drawing Sheets

Related U.S. Application Data

(60) Provisional application No. 62/237,848, filed on Oct. 6, 2015.

(51) Int. Cl.
```
A61L 27/10    (2006.01)
A61L 27/14    (2006.01)
A61L 27/54    (2006.01)
C25D 13/02    (2006.01)
C25D 13/12    (2006.01)
C25D 13/18    (2006.01)
C25D 15/00    (2006.01)
```
(52) U.S. Cl.
CPC ............ *A61L 27/54* (2013.01); *C25D 13/02* (2013.01); *C25D 13/12* (2013.01); *C25D 13/18* (2013.01); *C25D 15/00* (2013.01); *A61L 2300/102* (2013.01); *A61L 2300/606* (2013.01); *A61L 2400/12* (2013.01); *A61L 2420/02* (2013.01); *A61L 2430/02* (2013.01); *A61L 2430/24* (2013.01)

(58) Field of Classification Search
CPC ......... A61L 2300/102; A61L 2300/606; A61L 2400/12; A61L 2420/02; A61L 2430/02; A61L 2430/24; A61L 31/022; A61L 31/128; A61L 2420/04; A61L 2420/06; A61L 31/10; A61L 31/088; C25D 13/02; C25D 13/12; C25D 13/18; C25D 15/00; C25D 13/06; C25D 13/04; C25D 13/00; C25D 5/04; A61K 33/16; C01F 17/235; B82Y 30/00; B01J 23/10; B01J 35/23; C01B 15/01; C01P 2002/60; C01P 2004/64; C01P 2002/72; C01P 2004/61; C01P 2004/04

See application file for complete search history.

(56) References Cited

U.S. PATENT DOCUMENTS

| | | | |
|---|---|---|---|
| 7,534,453 | B1 | 5/2009 | Rzigalinski et al. |
| 11,007,303 | B2 | 5/2021 | Seal et al. |
| 2005/0107870 | A1 | 5/2005 | Wang et al. |
| 2007/0123996 | A1 | 5/2007 | Sugaya et al. |
| 2011/0059264 | A1 | 3/2011 | Park et al. |
| 2011/0135740 | A1 | 6/2011 | Sugaya et al. |
| 2021/0290822 | A1 | 9/2021 | Seal et al. |

OTHER PUBLICATIONS

Hamdi et al."Electrodeposition of Cerium Film Compound, Elaboration And Characterization", Lebanese Science Journal, vol. 10, No. 2, 2009, 71-80 (Year: 2009).*
Naganuma T, Traversa E. The effect of cerium valence states at cerium oxide 10 nanoparticle surfaces on cell proliferation. Biomaterials. 2014;35:4441-4453.
Noor Z, Kania N, Setiawan B. Tibia bone properties at different time course of ovariectomized rats. J Diabetes Metab Disord. 2014;13:91.
Novack DV, Teitelbaum SL. The osteoclast: friend or foe? Annu Rev pathmechdis Mech Dis. 2008;3:457-84.
Nyazee HA, et al., Diabetic foot osteomyelitis: Bone markers and treatment outcomes. Diabetes Res Clin Pract. 2012;97:411-417.
Olivares-Navarrete R, et al., Osteoblast maturation and new bone formation in response to titanium implant surface features are reduced with age. Journal of bone and mineral research: the official journal of the American Society for Bone and Mineral Research. 2012;27:1773-1783.
Pirih F, Lu J, Ye F, Bezouglaia O, Atti E, Ascenzi MG, Tetradis S, Demer L, Aghaloo T, Tintut Y. Adverse effects of hyperlipidemia on bone regeneration and strength. Journal of bone and mineral research: the official journal of the American Society for Bone and Mineral Research. 2012;27:309-318.
Pirmohamed T, Dowding JM, Singh S, Wasserman B, Heckert E, Karakoti AS, King JE, Seal S, Self WT. Nanoceria exhibit redox state-dependent catalase mimetic activity. Chemical communications. 2010;46:2736-2738.
Platt ID, Josse AR, Kendall CW, Jenkins DJ, El-Sohemy A. Postprandial effects of almond consumption on human osteoclast precursors—an ex vivo study. Metabolism. 2011;60:923-929.
Ponnusamy M, et al., Autophagy protects against necrotic renal epithelial cell-induced death of renal interstitial fibroblasts. American journal of physiology. Renal physiology. 2012;303:F83-91.
Purdue PE, Koulouvaris P, Nestor BJ, Sculco TP. The central role of wear debris in periprosthetic osteolysis. HSS journal : the musculoskeletal journal of Hospital for Special Surgery. 2006;2:102-113.
Rocca A, Moscato S, Ronca F, Nitti S, Mattoli V, Giorgi M, Ciofani G. Pilot in vivo investigation of cerium oxide nanoparticles as a novel anti-obesity pharmaceutical formulation. Nanomedicine : nanotechnology, biology, and medicine. 2015;11:1725-1734.
Rodriguez EK, Boulton C, Weaver MJ, Herder LM, Morgan JH, Chacko AT, Appleton PT, Zurakowski D, Vrahas MS. Predictive factors of distal femoral fracture nonunion after lateral locked plating: A retrospective multicenter casecontrol study of 283 fractures. Injury. 2014;45:554-559.
Scafonas A, et al., Agonist-like serm effects on eralpha-mediated repression of mmp1 promoter activity predict in vivo effects on bone and uterus. J Steroid Biochem Mol Biol. 2008;110:197206.
Schmidt A, et al., Identification of anabolic selective androgen receptor modulators with reduced activities in reproductive tissues and sebaceous glands. The Journal of biological chemistry. 2009;284:36367-36376.
Seong WJ, et al., Comparison of push-in versus pull-out tests on bone-implant interfaces of rabbit tibia dental implant healing model. Clin Implant Dent Relat Res. 2013;15:460-469.
Shao JS, Cheng SL, Charlton-Kachigian N, Loewy AP, Towler DA. Teriparatide (human parathyroid hormone (1-34)) inhibits osteogenic vascular calcification in diabetic low density lipoprotein receptor-deficient mice. The Journal of biological chemistry. 2003;278:50195-50202.
Shao JS, Cheng SL, Pingsterhaus JM, Charlton-Kachigian N, Loewy AP, Towler DA. Msx2 promotes cardiovascular calcification by activating paracrine wnt signals. The Journal of clinical investigation. 2005;115:1210-1220.
Shao JS, Sierra OL, Cohen R, Mecham RP, Kovacs A, Wang J, Distelhorst K, Behrmann A, Halstead LR, Towler DA. Vascular calcification and aortic fibrosis: A bifunctional role for osteopontin in diabetic arteriosclerosis. Arterioscler Thromb Vasc Biol. 2011;31:1821-1833.
Silva MJ. Biomechanics of osteoporotic fractures. Injury. 2007;38 Suppl 3:S69-76.
Soloviev A, Schwarz EM, Kuprash DV, Nedospasov SA, Puzas JE, Rosier RN, O'Keefe RJ. The role of p105 protein in nfkappab activation in ana-1 murine macrophages following stimulation with titanium particles. Journal of orthopaedic research : official publication of the Orthopaedic Research Society. 2002;20:714-722.
Sun N, Guo Y, Liu W, Densmore M, Shalhoub V, Erben RG, Ye L, Lanske B, Yuan Q. Fgf23 neutralization improves bone quality and osseointegration of titanium implants in chronic kidney disease mice. Scientific reports. 2015;5:8304.

(56) References Cited

OTHER PUBLICATIONS

Thompson B, Towler DA. Arterial calcification and bone physiology: Role of the bone-vascular axis. Nat Rev Endocrinol. 2012;8:529-543.
Towler DA, Bidder M, Latifi T, Coleman T, Semenkovich CF. Diet-induced diabetes activates an osteogenic gene regulatory program in the aortas of low density lipoprotein receptor-deficient mice. The Journal of biological chemistry. 1998;273:30427-30434.
Troiano NW, Ciovacco WA, Kacena MA. The effects of fixation and dehydration on the histological quality of undecalcified murine bone specimens embedded in methylmethacrylate. J Histotechnol. 2009;32:27-31.
Vaira S, Johnson T, Hirbe AC, Alhawagri M, Anwisye I, Sammut B, O'Neal J, Zou W, Weilbaecher KN, Faccio R, Novack DV. Relb is the nf-kappab subunit downstream of nik responsible for osteoclast differentiation. Proceedings of the National Academy of Sciences of the United States of America. 2008;105:3897-3902.
Vaira S, Alhawagri M, Anwisye I, Kitaura H, Faccio R, Novack DV. Rela/p65 promotes osteoclast differentiation by blocking a rankl-induced apoptotic jnk pathway in mice. The Journal of clinical investigation. 2008;118:2088-2097.
Walkey C, Das S, Seal S, Erlichman J, Heckman K, Ghibelli L, Traversa E, McGinnis JF, Self WT. Catalytic properties and biomedical applications of cerium oxide nanoparticles. Environ Sci Nano. 2015;2:33-53.
Wang Y, Wei M, Gao J, Hu J, Zheng Y. Corrosion process of pure magnesium in simulated body fluid. Materials letters. 2008;62:2181-2184.
Watts CD, Houdek MT, Wagner ER, Abdel MP, Taunton MJ. Insulin dependence increases the risk of failure after total knee arthroplasty in morbidly obese patients. The Journal of arthroplasty. 2015.
Windahl SH, Lagerquist MK, Andersson N, Jochems C, Kallkopf A, Hakansson C, Inzunza J, Gustafsson JA, van der Saag PT, Carlsten H, Pettersson K, Ohlsson C. Identification of target cells for the genomic effects of estrogens in bone. Endocrinology. 2007;148:5688-5695.
Wohl GR, Towler DA, Silva MJ. Stress fracture healing: Fatigue loading of the rat ulna induces upregulation in expression of osteogenic and angiogenic genes that mimic the intramembranous portion of fracture repair. Bone. 2009;44:320-330.
Wukich DK. Diabetes and its negative impact on outcomes in orthopaedic surgery. World J Orthop. 2015;6:331-339.
Yadav VR, Prasad S, Sung B, Aggarwal BB. The role of chalcones in suppression of nf-kappab-mediated inflammation and cancer. Int Immunopharmacol. 2011;11: 295-309.
Yang C, McCoy K, Davis JL, Schmidt-Supprian M, Sasaki Y, Faccio R, Novack DV. Nik stabilization in osteoclasts results in osteoporosis and enhanced inflammatory 15 osteolysis. PloS one. 2010;5:e15383.
Yang Y, et al., Controllable morphology and conductivity of electrodeposited cu(2)o thin film: Effect of surfactants. ACS Appl Mater Interfaces. 2014;6:22534-22543.
Yang X, Ricciardi BF, Dvorzhinskiy A, Brial C, Lane Z, Bhimani S, Burket JC, Hu 25 B, Sarkisian AM, Ross FP, van der Meulen MC, Bostrom MP. Intermittent parathyroid hormone enhances cancellous osseointegration of a novel murine tibial implant. The Journal of bone and joint surgery. American volume. 2015;97:10741083.
Yang Z, Liu H, Xie X, Tan Z, Qin T, Kang P. The influence of diabetes mellitus on the post-operative outcome of elective primary total knee replacement: A systematic review and meta-analysis. Bone Joint J. 2014;96-B:1637-1643.
Zou H, Zhao X, Sun N, Zhang S, Sato T, Yu H, Chen Q, Weber HP, Dard M, Yuan Q, Lanske B. Effect of chronic kidney disease on the healing of titanium implants. Bone. 2013;56:410-415. 38.
Ng, W.F. et al., "Cerium-based coating for enhancing the corrosion resistance of bio-degradable Mg implants", Material Chemistry and Physics, Feb. 2010, vol. 1 19, Issue 3, pp. 384-388.
PCT/US2016/055683; International Search Report and Written Opinion, Feb. 16, 2017, 18 pages.

Abu-Amer, Yousef et al., "Aseptic loosing of total joints replacement: mechanisms underlying osteolysis and potential therapies", Arthritis Research & Therapy 2007, 9(Suppl 1): S6 (doi:10.1186/ar2170).
Almeida, Maria et al., "Increased Lipid Oxidation Caused Oxidative Stress, Increased Peroxisome Proliferator-activated Receptor-y Expression, and Diminished Pro-osteogenic Wnt Singaling in the Skeleton", The Journal of Biological Chemistry, vol. 284, No. 40, pp. 27438-27488, Oct. 2, 2009.
Baier, Robert Edward, "Surface behaviour of biomaterials: The theta surface for biocompatibilty", J. Mater Sci: Mater Med (2006) 17: 1057-1062.
Beck, Ryan T. et al., "Review of Periprosthetic Osteolysis in Total Joint Arthroplasty: An Emphasis on Host Factors and Future Directions", Published online Sep. 15, 2011 in Wiley Online Library (wileyonlinelibrary.com).
Biswas, R.G. et al., "The Effects of a Ce02 Coating on the Corrosion Parameters of Type 304 Stainless Steel", JMEPEG (1998) 7:727-732.
Bolli, Roberto MD, "The New Circulation Research A Manifesto", Circ Res. 2010:106:216-226.
Cai, Xue et al., "Sustained inhibition of neovascularization in vldlr-/- mice following intravitreal injection of cerium oxide nanoparticles and the role of the ASK1-P38/JNK-NF-kB pathway", Biomatarerials, Jan. 2014; 35(1):249-25, doi:10.1016/j.biomaterials. 2013.10.022.
Cai, Xue et al., "Nanoceria and Thioredoxin Regulate a Common Antioxidative Gene Network in tubby Mice", Advances in experimental medicine and biology. 2014;801:829-836.
Cheng SL. et al., "Msx2 exerts bone anabolism via canonical wnt signaling", The Journal of biological chemistry. 2008;283:20505-20522.
Cheng SL. et al., "Activation of vascular smooth muscle parathyroid hormone receptor inhibits wnt/beta-catenin signaling and aortic fibrosis in diabetic arteriosclerosis". Circulation research. 2010;107:271-282.
Cheng SL. et al., "Dkk1 and msx2-wnt7b signaling reciprocally regulate the endothelial-mesenchymal transition in aortic endothelial cells". Arterioscler Thromb Vasc Biol. 2013;33:1679-1689.
Cheng SL. et al., "Targeted reduction of vascular msx1 and msx2 mitigates arteriosclerotic calcification and aortic stiffness in ldlr-deficient mice fed diabetogenic diets". Diabetes. 2014;63:4326-4337.
Cheng SL. et al., "Vascular smooth muscle lrp6 limits arteriosclerotic calcification in diabetic ldlr/-mice by restraining honcanonical wnt signals". Circulation research. 2015;117:142156.
Chigurupati S. et al., "Effects of cerium oxide nanoparticles on the growth of keratinocytes, fibroblasts and vascular endothelial cells in cutaneous wound healing". Biomaterials. 2013;34:2194-2201.
Cronin, James G. et al., "Toll-like Receptor 4 and MyD88 Dependent Signaling Mechanisms of the Innate Immune System are Essential for the Response to Lipopolysaccharide by Epithelial and Stromal Cells of the Bovine Endometrium", Biol Reprod. Feb. 2012 ; 86(2): 51.
Das, Soumen et al., "The induction of angiogenesis by cerium oxide nanoparticles through the modulation of oxygen in intracellular environments", Biomaterials 33 (2012) 7746-7755.
Das, Soumen et al., "Cerium oxide nanoparticles: applications and prospects in nanomedicine", Nanomedicine (2013) 8(9), 1483-1508.
Dempster DW et al., "Standardized nomenclature, symbols, and units for bone histomorphometry: A 2012 update of the report of the asbmr histomorphometry nomenclature committee", Journal of bone and mineral research: the official journal of the American Society for Bone and Mineral Research. 2013;28:2-17.
Dickinson BC et al., "A palette of fluorescent probes with varying emission colors for imaging hydrogen peroxide signaling in living cells", Journal of 5 the American Chemical Society. 2010;132:5906-5915.
Dowding JM et al., "Cerium oxide nanoparticles 10 scavenge nitric oxide radical (no)", Chemical communications. 2012;48:4896-4898.

(56) References Cited

OTHER PUBLICATIONS

Dowding JM et al., "Cellular interaction and toxicity depend on physicochemical properties and surface modification of redox-active nanomaterials", ACS nano. 2013;7:4855-4868.

Dowding JM et al., "Cerium oxide nanoparticles protect against abeta-induced mitochondrial fragmentation and neuronal cell death", Cell death and differentiation. 2014;21:1622-1632.

Faienza MF, et al., "Osteoclastogenic potential of peripheral blood mononuclear cells in cleidocranial dysplasia", Int J Med Sci. 2014;11:356-364.

Grosse S. et al., "Wear particles and ions from cemented and uncemented titanium-based hip prostheses-a histological and chemical analysis of retrieval material", Journal of biomedical materials research. Part B, Applied biomaterials. 2015;103:709-717.

Gupta, A. ett al., "Compression molded ultra high molecular weight polyethylene-hydroxyapatite-aluminum oxide-carbon nanotube hybrid composites for hard tissue replacement" Journal of Materials Science & Technology 2013;29:514-522.

Hamdy AS., "Advanced nano-particles anti-corrosion ceria based sol gel coatings for aluminum alloys", Materials Letters. 2006;60:2633-2637.

Heckert EG. et al., "The role of cerium redox state in the sod 5 mimetic activity of nanoceria", Biomaterials. 2008;29:2705-2709.

Heckman KL. et al., "Custom cerium oxide nanoparticles protect against a free radical mediated autoimmune degenerative disease in the brain", ACS nano. 2013;7:10582-10596.

Hirakawa K. et al., "Comparison and quantitation of wear debris of failed total hip and total knee arthroplasty", J Biomed Mater Res. 1996;31:257-263.

Hirst SM. et al., "Anti-inflammatory properties of cerium oxide nanoparticles", Small. 2009;5:2848-2856.

Hirst SM. et al., "Bio-distribution and in vivo antioxidant effects of cerium oxide nanoparticles in mice", Environmental toxicology. 2013;28:107-118.

Huang CH. et al., "Improvement of bio-corrosion resistance for ti42zr40si15ta3 metallic glasses in simulated body", Materials Science and Engineering C 52 (2015) 144-150.

Ishizaki T. et al., "Corrosion resistance and durability of superhydrophobic surface formed on magnesium alloy coated with nanostructured cerium oxide film and fluoroalkylsilane molecules in corrosive nacl aqueous solution", Langmuir: the ACS journal of surfaces and colloids. 2011;27:4780-4788.

Jepsen KJ. et al., "Establishing biomechanical mechanisms in mouse models: Practical guidelines for systematically evaluating phenotypic changes in the diaphyses of long bones", Journal of bone and mineral research: the official journal of the American Society for Bone and Mineral Research. 2015;30:951-966.

Jilka RL. et al., "Decreased oxidative stress and greater bone anabolism in the aged, when compared to the young, murine skeleton with parathyroid hormone administration", Aging cell. 2010;9:851-867.

Katagiri M. et al., "Mechanism of stimulation of osteoclastic bone resorption through gas6/tyro 3, a receptor tyrosine kinase signaling, in mouse osteoclasts", The Journal of biological chemistry. 2001;276:7376-7382.

Kayal RA, et al., "Diminished bone formation during diabetic fracture healing is related to the premature resorption of cartilage associated with increased osteoclast activity", Journal of bone and mineral research: the official journal of the American Society for Bone and Mineral Research. 2007;22:560-568.

Keegan GM. et al., "Orthopaedic metals and their potential toxicity in the arthroplasty patient: A review of current knowledge and future strategies", The Journal of bone and joint surgery. British volume. 2007;89:567-573.

Kilkenny C. et al., "Improving bioscience research reporting: The arrive guidelines for reporting animal research", Osteoarthritis and cartilage / OARS, Osteoarthritis Research Society. 2012;20:256-260.

Kim W-H. et al., "Growth characteristics and film properties of cerium dioxide prepared by plasma-enhanced atomic layer deposition", Journal of The Electrochemical Society 2011;158:G169-G172.

King, KB. et al., "Veterans with diabetes receive arthroplasty more frequently and at a younger age", Clinical orthopaedics and related research. 2013;471:3049-3054.

Korsvik C. et al., "Superoxide dismutase mimetic properties exhibited by vacancy engineered ceria nanoparticles", Chemical communications. 2007:1056-1058.

Kruger B. et al., "Isletexpressed tlr2 and tlr4 sense injury and mediate early graft failure after transplantation", European journal of immunology. 2010;40:2914-2924.

Kurtz S. et al., "Projections of primary and revision hip and knee arthroplasty in the united states from 2005 to 2030", The Journal of bone and joint surgery. American volume. 2007;89:780-785.

Lai CF. et al., "An osteopontin-nadph oxidase signaling cascade promotes pro-matrix metalloproteinase 9 activation in aortic mesenchymal cells", Circulation research. 2006;98:1479-1489.

Lai CF. et al., "Tnfr1-activated reactive oxidative species signals upregulate osteogenic msx2 programs in aortic myofibroblasts", Endocrinology. 2012;153:3897-3910.

Lung S, et al., "Brain suppression of ap-1 by inhaled diesel exhaust and reversal by cerium oxide nanoparticles", Inhal Toxicol. 2014;26:636-641.

McCormack RN. et al., "Inhibition of nanoceria's catalytic activity due to ce3+ site-specific interaction with phosphate ions", The Journal of Physical Chemistry C 2013;118:18992-19006.

Montemor MF. et al., "Chemical composition and corrosion protection of silane films modified with ceo 2 nanoparticles", Electrochimica Acta 2009;54:5179-5189.

Murphy LB. et al., "Arthritis Among Veterans—United States, 2011-2013", Morbidity and Mortality Weekly Report, 2014;63:999-1003.

* cited by examiner

IMPLANT AND COATING TO REDUCE OSTEOLYSIS

BACKGROUND

The American Academy of Orthopedic Surgeons has projected annual volumes of primary total hip joint replacement to increase over 748,000 in USA or 4 million worldwide by 2030. By 2030, total hip replacement surgery is expected to rise by 174% and total knee replacement by 673%. Despite technological advances and improvements in treatment strategies to manage rheumatoid arthritis and osteoarthritis, total joint replacement ("TJR") still remains the final treatment option in many cases to relieve pain, and improve the quality of life. Annual hospital costs associated with these procedures are projected to exceed $65 billion by 2015. However, due to osteolysis 10-15% TJR will fail, with some studies suggesting rates of osteolysis can approach 40%.

In the USA, the annual cost of TJR exceeds $10 billion. Although joint replacement surgery has made remarkable progress, 10-15% arthroplasty failure still occurs due to high levels of free radicals, chronic inflammation and osteolysis. In 2000, 28,000 and 31,000 revision surgeries were performed for total hip arthroplasty and total knee arthroplasty, respectively and the numbers of revision surgeries are increasing each year. Revision surgeries are 40% more costly than primary total hip and knee arthroplasties and more than 1 billion dollars are spent on revision surgeries each year alone in USA. At this time, there is no drug or treatment strategies specifically approved for prevention or inhibition of periprosthetic osteolysis (hereinafter "osteolysis").

Cerium is a rare-earth element with fluorite lattice structure with +3+4 oxidation states and may interchange between the two depending on the environment. Cerium oxide nanoparticles (hereinafter "CNP"s) have been shown to possess a substantial oxygen storage capacity via the interchangeable surface reduction and oxidation of cerium atoms, cycling between the $Ce^{4+}$ and $Ce^{3+}$ redox states. CNPs have a mixed oxidation state of cerium containing both $Ce^{3+}$ and $Ce^{4+}$. It has been shown that upon incubation of CNPs with hydrogen peroxide, CNPs with a higher starting concentration of $Ce^{3+}$ can convert to CNPs containing increased $Ce^{4+}$ on their surface. Along with this change in oxidation state is the loss of their SOD mimetic ability. However, increased $Ce^{4+}$ on the CNP surface exhibit better catalase mimetic and .NO scavenging capabilities.

It has been well established in many studies that depending on their reactivity and surface chemistry, CNPs can effectively convert both reactive oxygen species (ROS) (superoxide, $O_2^{.-}$, and hydrogen peroxide) into more inert species and scavenge reactive nitrogen species (RNS)(nitric oxide, .NO), both in vitro and in vivo. It has been further shown that CNPs significantly accelerate the decay of $ONOO^-$ and that CNPs ability to interact with $ONOO^-$ is independent of the $Ce^{3-}/Ce^{4+}$ ratio on the surface of the CNPs.

Due to these capabilities, these materials have been employed for industrial use in three-way catalysts. Biological uses of CNPs have centered on their ability to scavenge free radicals under physiologically relevant conditions. This catalytic nature, which began with the discovery that water-based CNPs (with increased $Ce^{3+}$ in their outer surface) could act as superoxide dismutase mimetics, has laid the foundation for their application in experimental and biomedical research.

CNPs are known for their regenerative antioxidant activity in a biological environment. The unique regenerative property of CNPs is due to low reduction potential and the existence of both $Ce^{3+}/Ce^{4+}$ oxidation states. It has been shown that the oxygen vacancies could act as catalytically active hot spots to scavenge very reactive radicals such as superoxide radical anion, hydrogen peroxide, nitric oxide or peroxynitrite. It has been shown that NC with higher levels of cerium in the +3 oxidation state exhibit superoxide dismutase activity and that this reactivity correlates with the level of cerium in the +3 oxidation state in a reversible manner. Likewise, NC with higher levels of surface cerium in the +4 oxidation state exhibit better catalase mimetic activity that also is reduced when higher levels of cerium are present in the +3 oxidation state.

DETAILED DESCRIPTION

Figure 1:
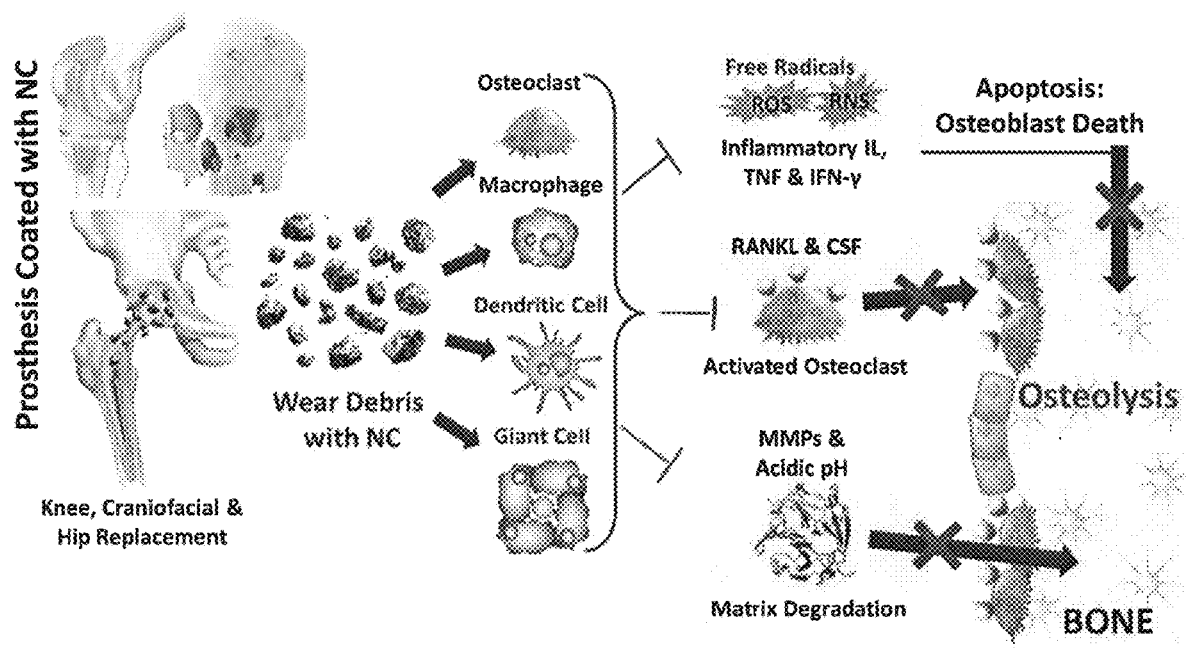
FIG. 1 is a schematic showing the mechanisms by which a NC coating can prevent osteolysis by scavenging free radicals, suppressing immune reaction locally and inhibiting corrosion, in accordance with an embodiment.

Total joint replacement and the use of prostheses/implants are rapidly growing due to higher life expectancy and the growing obesity epidemic. However, 10-15% of implants will fail and will need extensive revision surgery mainly due to osteolysis. At this time, there are no drug or treatment strategies specifically approved for prevention or inhibition of periprosthetic osteolysis.

It was previously unknown whether coating forms of CNPs would exhibit the same catalytic activity described above. One concern was the ability to create a coating which retained the catalytic and radical scavenging properties described above and in the cited references, as previous studies involved CNPs. In contrast, a nanoceria ("NC") coating is provided herein that is formed on a substrate (or on an intermediate layer between the substrate and the coating) and as such, no longer in nanoparticle form. It is shown through experiments described below the NC coatings developed and disclosed retain the catalytic mimetic activities reported for the CNPs. Moreover the NC coatings enhance osseointegration, and reduce overall osteolysis. Both methods and products are disclosed.

As to the methods, embodiments disclosed include making an implant comprising the steps of obtaining a substrate comprising materials comprised in whole or in part of metal, ceramic, plastic, or a composite; and depositing a nanoceria coating on at least a portion of the substrate, wherein the nanoceria coating has a predetermined surface roughness parameter and a surface cerium 3+/4+ oxidation state ratio such that said nanoceria coating exhibits catalase mimetic activity, superoxide dismutase mimetic activity, or both. In these and other embodiments, the implant is adapted for the prevention or inhibition of osteolysis.

Embodiments described herein are based on the discovery that a significant cause of arthroplasty failure occurs due to high levels of free radicals, chronic inflammation and osteolysis. Osteolysis is the destruction of bone tissue. This may occur due to chronic inflammation from particles or debris generated through wear, electrochemical dissolution/corrosion, or a combination thereof. The implant coated at least partially thereon with an NC coating is able to reduce the presence of such free radicals and thus overall inflammation and osteolysis. Therefore, a method is also disclosed for reducing degradation of an implant by placing nanoceria in proximity to a bone-implant interface.

Further embodiments include an implant, or component of an implant, having said NC coating. As used herein, the term "component" refers to a part of an overall implant, bone implant, or other prosthesis. These implants comprise a NC coating on at least a portion thereof. In such an embodiment, the implant comprises at least a substrate on which an NC coating is coated; there may also be an intermediate layer between the coating and the substrate. Also disclosed are embodiments relating to a coating itself, without respect to any substrate or intervening layer upon which the coating may be disposed. The NC coatings of embodiments have various features. Namely, the coating is characterized by nanoceria having a surface cerium 3+/4+ oxidation state ratio such that such that the coating exhibits catalase mimetic activity, superoxide dismutase mimetic activity, or both.

Because cell attachment and proliferation of macrophage cells (involved in the osteolytic process) were shown to be inversely proportional with increasing roughness of the coating, the coatings disclosed may also have a predetermined surface roughness (described below). Methods for electrdeposition of an NC coating on a substrate are also disclosed. Broadly, a method comprises electrophoretically forming the coating on a given substrate using a dispersion of CNPs, preferably where the substrate is placed between two counter electrodes (for a total of three electrodes). However, a two electrode setup may also be used. This coating method uses CNPs having surface cerium in the 3+ oxidation state or 4+ oxidation state, or both, and results in an NC coating which has a given 3+/4+ ratio such that the desired and above described anti-inflammatory properties are exhibited. Coatings with both oxidation states are preferable, but either oxidation state imparts advantageous benefits.

According to another embodiment, a method is provided for conducting an orthopedic procedure in a subject in need thereof. The method involves obtaining an implant having an NC coating as described herein and implanting the implant into the subject at a site of need. The implantation involves positioning the implant so as to have contact with bone tissue. In a specific embodiment, the orthopedic procedure is an arthroplasty procedure, and the implant is one for insertion in or between a joint. Examples of arthroplasty implants include hip replacement implants, knee replacement implants, shoulder replacement, and intervertebral implants. Other related orthopedic implants that may be coated and used in accordance with the embodiments described herein include, but are not limited, plates, screws, rods, cages, dowels and the like used in orthopedic surgeries. A subject as used herein refers to a mammal including but not limited to a human, dog, cat, horse, goat, cow etc. A subject in need is one who has an injury, defect or disease of the musculoskeletal system requiring an orthopedic surgery.

Furthermore, based on the discoveries herein, an alternative embodiment relates to a bone paste composition that includes CNPs comprising catalase activity, superoxide dismutase activity, or both, and at least one osteoinductive or osteoconductive component. Examples of osteoinductive or osteoconductive components include, but are not limited to, demineralized bone powder as described in U.S. Pat. No. 5,073,373 the contents of which are incorporated herein by reference, collagen, insoluble collagen derivatives, hydroxyapatite, ceramic, calcium phosphate, dicalcium phosphate, tricalcium phosphate, bone morphogentic protein, transforming growth factor (TGF-beta), insulin-like growth factor (IGF-1) (IGF-2), platelet derived growth factor (PDGF), fibroblast growth factors (FGF), vascular endothelial growth factor (VEGF), angiogenic agents, bone promoters, cytokines, interleukins, genetic material, genes encoding bone promoting action, cells containing genes encoding bone promoting action; growth hormones such as somatotropin; bone digestors; antitumor agents; fibronectin; cellular attractants and attachment agents. U.S. Pat. No. 6,695,882, incorporated by reference, teaches other osteoinductive and osteoconductive components.

In a further embodiment, the bone paste includes a suitable carrier component. Examples of carrier components include, but are not limited to:
(i) Polyhydroxy compound, for example, such classes of compounds as the acyclic polyhydric alcohols, non-reducing sugars, sugar alcohols, sugar acids, monosaccarides, disaccharides, water-soluble or water dispersible oligosaccharides, polysaccharides and known derivatives of the foregoing. Specific polyhydroxy compounds include, 1,2-propanediol, glycerol, 1,4-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, e.g., of the type known and commercially available under the trade names Pluronic and Emkalyx; polyoxyethylene-polyoxypropylene block copolymer, e.g., of the type known and commercially available under the trade name Poloxamer; alkylphenolhydroxypolyoxyethylene, e.g., of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing, and the like.

(ii) Polyhydroxy ester, for example, liquid and solid monoesters and diesters of glycerol can be used to good effect, the solid esters being dissolved up to the limit of their solubilities in a suitable vehicle, e.g., propylene glycol, glycerol, polyethylene glycol of 200-1000 molecular weight, etc. Liquid glycerol esters include monacetin and diacetin and solid glycerol esters include such fatty acid monoesters of glycerol as glycerol monolaurate, glyceryl monopalmitate, glyceryl monostearate, etc. An especially preferred carrier herein comprises glyceryl monolaurate dissolved in glycerol or a 4:1 to 1:4 weight mixture of glycerol and propylene glycol, poly(oxyalkylene) glycol ester, and the like.

(iii) Fatty alcohol, for example primary alcohols, usually straight chain having from 6 to 13 carbon atoms, including caproic alcohol, caprylic alcohol, undecyl alcohol, lauryl alcohol, and tridecanol.

(iv) Fatty alcohol ester, for example, ethyl hexyl palmitate, isodecyl neopentate, octadodecyl benzoate, diethyl hexyl maleate, and the like.

(v) Fatty acid having from 6 to 11 carbon atoms, for example, hexanoic acid, heptanoic acid, octanoic acid, decanoic acid and undecanoic acid.

(vi) Fatty acid ester, for example, polyoxyethylene-sorbitan-fatty acid esters; e.g., mono- and tri-lauryl, palmityl, stearyl, and oleyl esters; e.g., of the type available under the trade name Tween from Imperial Chemical Industries; polyoxyethylene fatty acid esters; e.g., polyoxyethylene stearic acid esters of the type known and commercially available under the trade name Myrj; propylene glycol mono- and di-fatty acid esters such as propylene glycol dicaprylate; propylene glycol dilaurate, propylene glycol hydroxy stearate, propylene glycol isostearate, propylene glycol laureate, propylene glycol ricinoleate, propylene glycol stearate, and propylene glycol caprylic-capric acid diester available under the trade name Miglyol; mono-, di-, and mono/di-glycerides, such as the esterification products of caprylic or caproic acid with glycerol; e.g., of the type known and commercially available under the trade name Imwitor; sorbitan fatty acid esters, e.g., of the type known and commercially available under the trade name Span, including sorbitan-monolauryl, -monopalmityl, -monostearyl, -tristearyl, -monooleyl and triolcylesters; monoglycerides, e.g., glycerol mono oleate, glycerol mono palmitate and glycerol monostearate, for example as known and commercially available under the trade names Myvatex, Myvaplex and Myverol, and acetylated, e.g., mono- and di-acetylated monoglycerides, for example, as known and commercially available under the trade name Myvacet; isobutyl tallowate, n-butylstearate, n-butyl oleate, and n-propyl oleate. (vii) Liquid silicone, for example, polyalkyl siloxanes such as polymethyl siloxane and poly(dimethyl siloxane) and polyalkyl arylsiloxane.

Other additives to the bone paste are taught in WO2005/110437 incorporated herein by reference (see for example claim 31). Examples of bone paste additive materials include polymers such as polylactones, polyamines, polymers and copolymers of trimethylene carbonate with any other monomer, vinyl polymers, acrylic acid copolymers, polyethylene glycols, polyethylenes, Polylactides; Polyglycolides; Epsilon-caprolactone; Polylacatones; Polydioxanones; other Poly(alpha-hydroxy acids); Polyhydroxyalkonat.es; Polyhydroxybutyrates; Polyhydroxyvalerates; Polycarbonates; Polyacetals; Polyorthoesters; Polyamino acids; Polyphosphoesters; Polyesteramides; Polyfumerates; Polyanhydrides; Polycyanoacrylates; Poloxamers; Polysaccharides; Polyurethanes; Polyesters; Polyphosphazenes; Polyacetals; Polyalkanoates; Polyurethanes; Poly(lactic acid) (PLA); Poly(L-lactic acid) (PLLA); Poly (DL-lactic acid); Poly-DL-lactide-co-glycolide (PDLGA); Poly(L-lactide-co-glycolide) (PLLGA); Polycaprolactone (PCL); Poly-epsilon-caprolactone; Polycarbonates; Polyglyconates; Polyanhydrides; PLLA-co-GA; PLLA-co-GA 82:18; Poly-DL-lactic acid (PDLLA); PLLA-co-DLLA; PLLA-co-DLLA 50:50; PGA-co-TMC (Maxon B); Polyglycolic acid (PGA); Poly-p-dioxanone (PDS); PDLLA-co-GA; PDLLA-co-GA (85:15); aliphatic polyester elastomeric copolymer; epsilon-caprolactone and glycolide in a mole ratio of from about 35:65 to about 65:35; epsilon-caprolactone and glycolide in a mole ratio of from about 45:55 to about 35:65; epsilon-caprolactone and lactide selected from the group consisting of L-lactide, D-lactide and lactic acid copolymers in a mole ratio of epsilon-caprolactone to lactide of from about 35:65 to about 65:35; Poly(L-lactide and caprolactone in a ratio of about 70:30); poly (DL-lactide and caprolactone in a ratio of about 85:15); poly(DL-lactide and caprolactone and glycolic acid in a ratio of about 80:10:10); poly(DL-lacticde and caprolactone in a ratio of about 75:25); poly (L-lactide and glycolic acid in a ratio of about 85:15); poly(L-lactide and trimethylene carbonate in a ratio of about 70:30); poly(L-lactide and glycolic acid in a ratio of about 75:25); Gelatin; Collagen; Elastin; Alginate; Chitin; Hyaluronic acid; Aliphatic polyesters; Poly(amino acids); Copoly(ether-esters); Polymethyl methacrylate (PMMA), Polyalkylene oxalates; Polyamides; Poly(iminocarbonates); Polyoxaesters; Polyamidoesters; Polyoxaesters containing amine groups; and Poly(anhydrides). The polymer can also be copolymer or terpolymer. It can be a blend of two or more individual substances mixed together. Accordingly, bone paste embodiments may include CNPs and one or more osteoinductive and/or osteoconductive components, and optionally a carrier component and/or a bone paste additive component.

FIG. 1 shows a schematic of mechanisms by which osteolysis is thought to occur. Large debris (20-100 μm) leads to "frustrated phagocytosis" which activates the NALP3 inflammasome via increases in reactive oxygen species (ROS) and reactive nitrogen species (RNS).

Whereas smaller particles (<10 μm) activate the NALP3 inflammasome by destabilizing endosome and leaking cathepsins into the cytoplasm[5]. The level of both mRNA and secreted pro-inflammatory cytokines such as IL-1, IL-6, IL-12, tumor necrosis factor (TNF) and receptor activator of nuclear factor κB ligand (RANKL) [5-8] were reported higher in bone-prosthesis interface tissue. RANKL and macrophage colony-stimulating factor (M-CSF) are also known to involve in maturation of osteoclast progenitors into multinucleated osteoclasts which are involved in bone dissolution. It has been reported that tissues collected at the bone-prosthesis interface had increased levels of both mRNA and secreted pro-inflammatory cytokines such as IL-1, IL-6, IL-12, TNF and RANKL.

FIG. 1 illustrates these processes and the manner in which the NC coated components prevent or inhibit these processes. The following pathways were identified for osteolysis: 1. De novo osteoclastogenesis, which occurs in response to the release of M-CSF and RANKL 2. Induction of osteoblasts apoptosis; and 3. Secretions of the matrix metalloproteinases (MMPs), collagenases and tissue-processing enzymes during the inflammatory process.

The inventors herein have developed a nanoceria coating having regenerative antioxidant activity in biological microenvironment and can scavenge free radicals and suppress immune reaction/osteoclast activation which may inhibit the osteolysis, and prevent/delay implant failure. The coating which may be coated on a substrate to produce an implant. The substrate may be a prosthesis in embodiments.

The degree of catalytic activity may be varied by varying the $Ce^{3+}/Ce^{4+}$ ratio on the surface cerium of the CNPs used to manufacture the NC coating, and as a function of the coating parameters utilized in preparing the NC coating. The coating on an implant retains the catalytic activity of the CNPs.

Other embodiments include methods for assembling CNPs on the surface of Ti (and other metal alloys, such as CoCrMo) such that an NC coating is formed to retain the ROS/RSN catalytic properties that convey anti-inflammatory properties. The presence of NC in the milieu of the prosthetic-bone interface enhances osseous integration. This is shown via studies of the impact of nanoceria-coated titanium on NFkB-dependent osteoclast differentiation, activation, and bone resorption, using RANKL-stimulated human osteoclast progenitors and bone resorption as a model for study.

The NC coatings disclosed enable nanoceria-dependent collapse of ROS/RNS accumulation in response to inflammatory stimulants on susbtrates such as titanium. Pulse electrophoretic deposition (EPD) is used to provide a homogeneous coating on metal substrates with better catalytic activity. This coating allows better cell attachment and growth than known implant surfaces.

Figure 2:
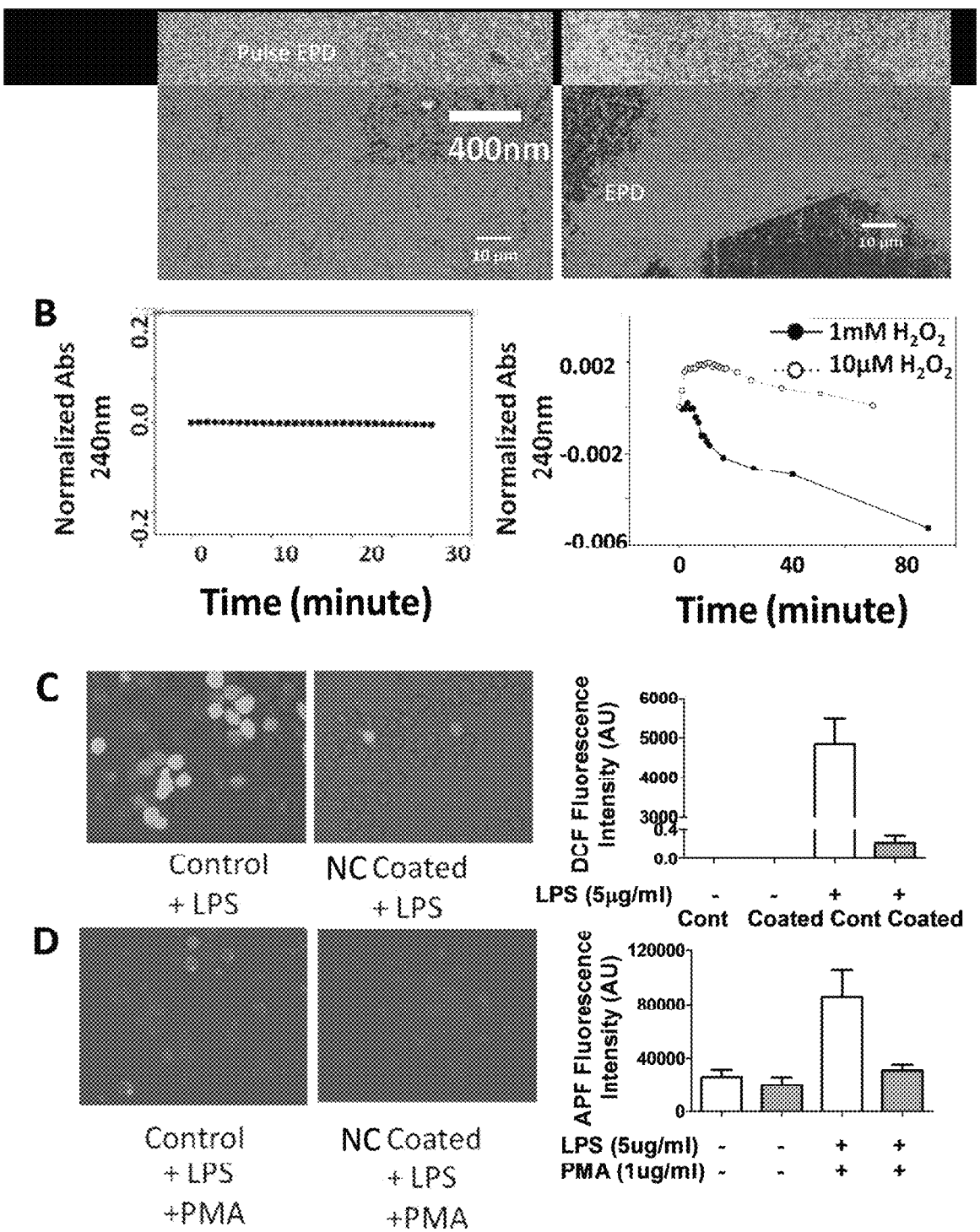
FIG. 2 shows topology and catalytic properties of the NC coating. (A) Surface morphology of EPD coated NC (left—pulse EPD; right—direct current) in accordance with an embodiment; B) Real time degradation of $H_2O_2$ followed absorbance at 240 nm; (C) ROS estimated using $H_2DCF$ fluorescence in an NC coated substrate in accordance with an embodiment; and (D) RNS using APF fluorescence assay in an NC coated substrate, in accordance with an embodiment.

FIG. 2 shows data for the topology and catalytic property of the NC coating. NC was coated on Ti substrate using pulse EPD and EPD. FIG. 2A shows pulse EPD (left) and EPD (right) using NC. FIG. 2A shows surface morphology of the EPD coated Ti substrate (left-pulse EPD; right-direct current). The results show EPD resulted in a more homogeneous coating compared to EPD.

Coatings and their method of preparation are disclosed. The coatings may have NC with varying ratios of surface cerium in the $Ce^{3+}$ and $Ce^{4+}$ oxidation state. Alternatively, the coating may have CNPs with surface cerium of only one valence state, although a mixture of oxidation states is preferable. The coatings may be used to coat any compatible substrate or prosthesis. Modes disclosed involve the coating of Ti and CoCrMo substrates. As mentioned above, first nanoparticles (NP) are produced. Embodiments disclosed are (a) NC with cerium predominantly in the $Ce^{3+}$ oxidation state (NC1) and (b) NC with cerium predominantly in the $Ce^{4+}$ oxidation state higher (NC2). However it is understood that coatings formed from these nanoparticles (using methods below, for e.g.) can have both NC 1 and N2. Alternatively coatings may be formed from either NC1 or NC2.

1. Preparation of Different $Ce^{3+}/Ce$ Nanoparticles ("QNP")

Cerium is a rare-earth element with fluorite lattice structure with +3+4 oxidation states and may interchange between the two oxidation states depending on the environment. Surface Ce3+/Ce4+ ratio of nanoparticles of this material is also known to depend on size of the nanoparticles. Agglomeration free and smaller size nanoparticles will also determine the quality of the coating and topology of the coating.

As mentioned above, to produce the coating using the disclosed methods, first cerium nanoparticles (CNP) are provided. In certain embodiments, CNPs of 3-5 nm size with different surface Ce3+/C34+ ratios are synthesized. The CNPs are then deposited on the surface of an implant grade titanium substrate (forming a nanoceria substrate also referred to herein as "NC coating"). The NC coating will no longer contain ceria in nanoparticle form. It was not previously known whether NC coatings retained the same catalytic activities that were reported for CNPs. Specific techniques for depositing the CNPs were developed and disclosed herein.

CNPs are made by several different methods, including precipitation, attrition, pyrolysis (including ultrasonic nozzle spray pyrolysis) and hydrothermal synthesis with thermal plasma or with other plasmas, such as with an RF induction plasma torch. Any of these methods, or any methods known in the art can be used for CNP production. The particles can be characterized using common laboratory techniques, including various forms of electron microscopy known in the art, atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser methods such as MOLDI-TOF, nuclear magnetic resonance (NMR), or any other convenient method known in the art. Nano-tracking analysis (NTA) can be used to detect the particles' Brownian motion and therefore allows sizing of nanoparticles in solution.

CNPs produced herein are preferably used in an electrolyte for pulse electrodeposition onto a substrate. Therefore, CNPs are first produced before implementation into a coating process. CNPs may be synthesized having surface cerium with different ratios of oxidation state: (a) CNPs with higher $Ce^{3+}$ ("NC1") (more 3+ than 4+) on the particle surface and (b) CNPs with higher $Ce^{4+}$ ("NC2") (more 4+ than 3+) on the particle surface. However it is understood that coatings formed from these nanoparticles (using methods below, for example) can have both NC1 and NC2. Alternatively, coatings may be formed from either NC1 or NC2. According to a specific example, NC1 and NC2 may be synthesized using wet chemical method, maintaining sterile environment using high purity (99.999%) cerium nitrate hexa hydrate precursor.

Bare and surface-modified CNPs are engineered by simple wet chemical methods wherein a precursor chemical (such as cerium nitrate) is oxidized in a controlled environment to yield CNPs. The redox property and oxygen buffering capacity of CNPs are governed by the surface Ce3+/Ce4+ ratio. Transmission Electron Microscopy (TEM) and Dynamic Light Scattering (DLS) are used to determine the size and hydrodynamic size of NPs.

Figure 3:
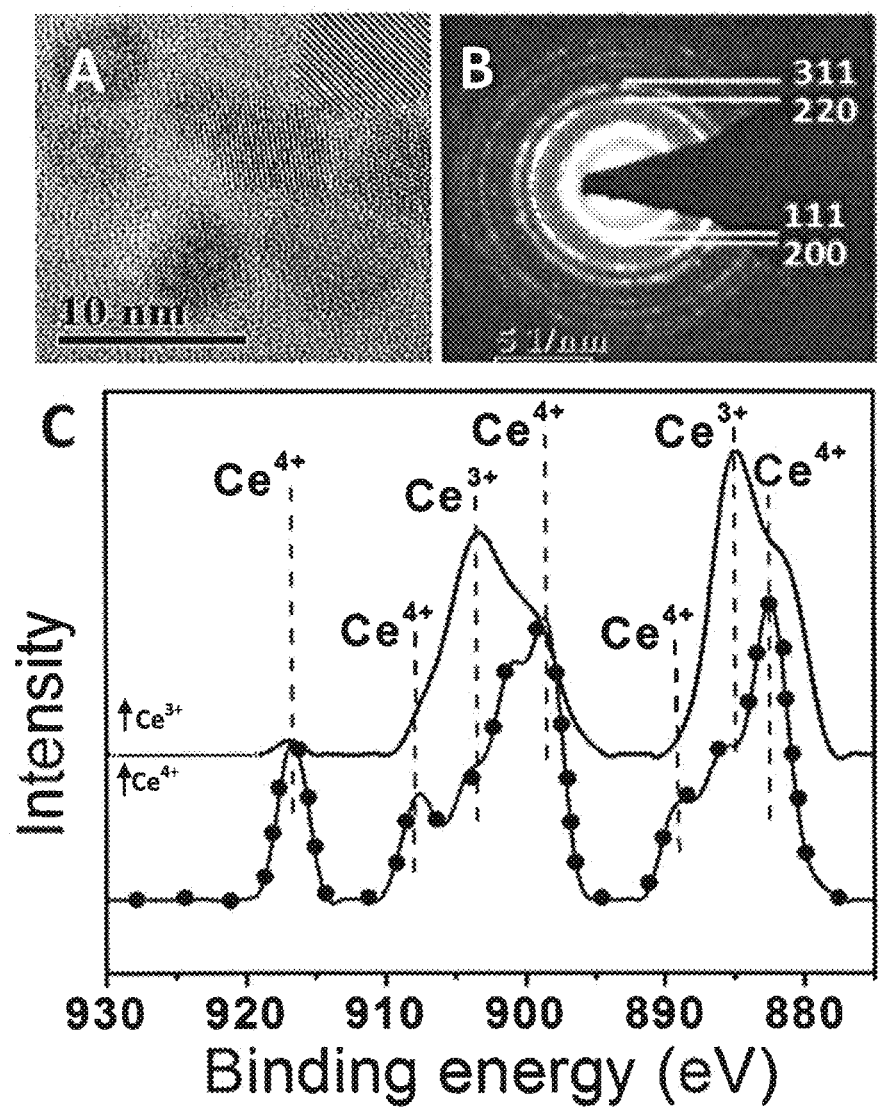
FIG. 3 shows (A) HRTEM images of NC1.3-5 nm NC1; (B) the interplanar spacing of lattice, representation of fluorite structure of NC (selected area diffraction pattern). (C) XPS spectra show variation in Ce3+/Ce4+ in two different NC (solid line NC1; sphere-NC2).

FIG. 3 shows (A) HRTEM images of NC1; 3-5 nm NC1; (B) the interplanar spacing of a lattice representation of fluorite structure of CNPs (selected area diffraction pattern) (C) XPS spectra showing variation in Ce3+/Ce4+ in two different CNPs (solid line NC1; sphere NC2). 3-5 nm particles are preferably produced (FIG. 3A) and tested for physicochemical properties prior to forming the coating.

As mentioned earlier, CNP size and morphology is very important for catalytic activity as well as the coating morphology. Size and morphology of the starting nanoparticle will be analyzed using high-resolution transmission electron microscope (HRTEM) and dynamic light scattering instrument (DLS). HRTEM will provide the morphology and size of the nanoparticles. Selected area diffraction pattern (SAED) is collected to reveal the crystalline structure. Particles hydrodynamic size/agglomeration are measured using DLS in both water and ethanol (ethanol will be used for pulse EPD). Crystallinity of the nanoparticle are analyzed using selected area electron diffraction and X-Ray diffraction (XRD). Surface $Ce^{3+}/Ce^{+4}$ ratios are analyzed by Electron energy-loss spectroscopy and X-ray photoelectron spectroscopy (XPS). XPS survey spectrum is used to determine the surface impurity of the nanoparticles, if any.

Surface properties of the nanoparticles are very important as electrophoretic mobility of the nanoparticles directly influence the deposition of the nanoparticles into an NC coating. Surface charge of the nanoparticles is estimated using zeta potentiometer. Hydrogen peroxide, superoxide and nitric oxide radical scavenging activity is confirmed using known assay established by the inventors herein[23] to test redox activity of the nanoparticles.

2. Preparation of Coatings

Hydrophilic surface of the cerium oxide supports the initial cell attachment and proliferation of the human mesenchymal stem cells. Therefore, a coating may be synthesized with varying pulse EPD parameters with NC1 and NC2. If depositing the CNPs via electrodeposition (described below), the dispersion contains these CNP's, usually suspended around the portion of the substrate desired to be coated and counter electrode(s). In embodiments, the coating is synthesized with NC1 or NC2, and using varying pulse EPD parameters. Because the 3+ and 4+ oxidation states exhibit different modes of catalytic activity and anti-inflamatory properties, coatings having either form or both forms exhibit various levels of catalytic activity.

In an example, two different Ti materials are coated, but it is understood that other metals or appropriate substrates may be used. In this example, a Ti-substrate (dimension: 5 mm×5 mm & 2 mm×1 mm) and Ti-Particles (<0.1 μm and <1 μm) are used. EPD coating has been well established in the past few years for biomedical coatings. The technique is easy to implement, low-cost, fast, and can be used to make conformal coatings.

Example. Pulse EPD to Coat Substrate to Form a NC Coating/Design of the Counter Electrode Methods for using pulse EPD to coat an implant grade Ti substrate are disclosed. EPD (not pulse) may also be employed. Advantages of pulse EPD disclosed are a more uniform deposition, as explained above with reference to FIG. 2A.

One of the major challenges lies in the uniform coating of CNPs on the difficult geometries of implant and controlling the surface chemistry. It is recognized this is overcome in EPD by ensuring uniform electric field intensity in the proximity to the substrate. The novelty of EPD lies in the design, construction and placement of counter electrode (anode) in the electrolytic cell which will vary as a function Ti implant shape. As demonstrated in FIG. 8, the electric field intensity in a 3 electrode setup became significantly more uniform on either sides of cathode as compared to a 2 electrode setup (uniformity is demonstrated by the larger lighter area in the 3 electrode configuration). Finite elemental modeling using COMSOL is implemented to control the counter electrode design & EPD parameters to prepare coatings with the desired coating properties.

Figure 8A:
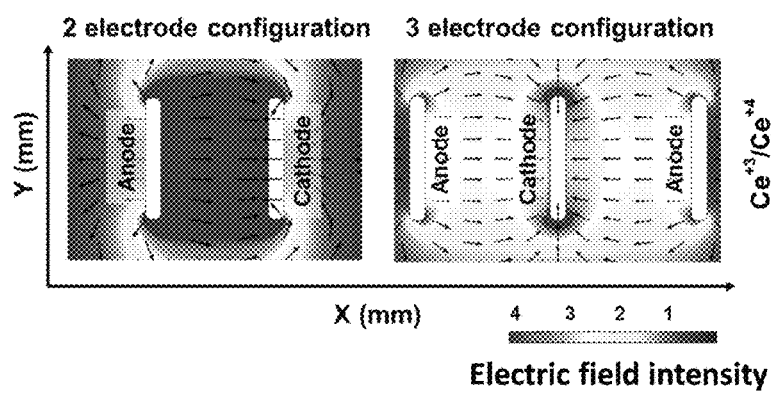
FIG. 8A shows an electric field simulation in a two v. three electrode configuration.
Figure 8B:
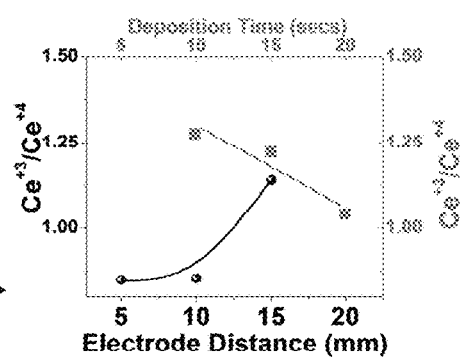
FIG. 8B is a graph showing the coating Ce3+/Ce4+ ratio as a function of electrode distance and time, in accordance with an embodiment.

FIG. 8 demonstrates the electrode design. (A) Electric field simulation in a two v. three electrodes configuration (arrow showing NC movement) (B) Coating $Ce^{3+}/Ce^{4+}$ ratio as a function of electrode distance and time. Additionally, the selection of process parameters in EPD allows the flexibility to control the surface chemistry of cerium oxide i.e. whether Ce+3/Ce+4 or a desired ratio of each. The data of FIG. 8B shows that altering electrode distance and higher deposition time results in the altering Ce+3/Ce+4 ratio for the deposited coating. Because the two different charged species (Ce+3 v. Ce+4) work in different modes of anti-inflammation, the ability to create coatings having either one or both charges present helps enhance the bio-catalytic property of the coating. Moreover, the inventors have determined certain parameters may be used to obtain various Ce+3/Ce+4 ratios, e.g, the time and distance information in FIG. 8B which results in various ratios. The square data points are Ce3+/Ce4+ ratio to deposition time; round data is Ce3+/Ce4+ ratio to electrode distance. As a specific example, coatings may be prepared using 5 to 10 V, 1 cm distance, for 20 seconds, 1 sec pulse having surface cerium charge ratios ranging from Ce+3/Ce+4 ratios between (2.3-1.2).

In EPD, coating morphology is governed by the arrangement of 2-D clusters and yields coatings with varying roughness. By varying EPD parameters (current density and time) collectively 'm (mass deposited on the electrode; equation 1 & 2, below), the size of 2-D clusters and stacking nanoparticles one can achieve an optimum catalytic activity (catalase mimetic activity expressed in $K_{cat}$) and coating surface roughness (Root Mean Square roughness—$R_q$).

The mass of the deposited NC (m) on substrate is calculated using equation 1 & 2, $$h(t) = \frac{w_0}{V\rho}\mu_e(E - \Delta E)t \tag{1}$$

$$m(t) = A\frac{VD_d}{I_o\rho_d}[(1 + \alpha t)^{1/2} - 1] \tag{1}$$

$$\alpha = \frac{2KI_o^2}{V}\left(\frac{\rho_d}{D_d}\right) \tag{2}$$

where, $i_0$, current density time t=0, K, the deposited mass-passed charge ratio, V, the external applied voltage, $\rho_d$ and $D_d$, resistivity and density of the deposited layer. The catalytic activity may be enhanced by increasing the surface area of the coating as well as morphology/size and stacking of 2-D clusters. A regression model is developed to form an analytical relationship of "m" as a function of "$K_{cat}$" and "$R_q$". (m=f ($K_{cat}$, $R_q$)).

Using pulse EPD at various parameters, an NC coated substrate with varying physical and chemical parameters may therefore be developed. For example, the Ce3+/Ce4 ratio desired may be prepared using the time and electrode distance settings set forth in FIG. 8B. Note substrates of various sizes may be employed and a similar model used to obtain the ratios, thicknesses, and properties desired.

Synthesized nanoceria NC1 and NC2 both are positively charged (data not shown), therefore a cathodic EPD is employed. (If surface charge of NC is negative/or near neutral, acid treatment is used to modify the surface charge of the NC for better coating.) Platinum may be used as an anode, but other counter-electrode materials may be used. Different NC coatings (including coating thickness) are developed by varying nanoparticles concentrations (5 mM and 10 mM), pH (5 & 6), electrical field (0.5 V to 5 V) and time (pulse—1 and 5 sec).

In addition, Ti particles may be coated. Ti-particles (<0.1 µm and <1 µm) are coated with NC using pulse EPD in embodiments. The inventors herein have recognized the significance of coating particles of Ti is that Ti forms debris due to wear and tear. Debris generated for Ti are less than 10 µm and sometimes sub-nm, therefore <0.1 µm and <11 µm Ti particles may be coated.

For particle coatings, Ti-particles will be first dip coated on top of the Ti-electrode and then NC will be coated using pulse current. Moreover, a set of Ti-particles will also be coated using simple dip coating method and will be compared with EPD coated particles for catalytic activity. NC-coated Ti-particles will be selected for Aim 2 based on catalytic activity of the particles. Ti-Particles coated with NC will be used to model debris particles partially/fully coated with NC and will be used in bone resorption model.

A range of EPD parameters are disclosed. An electrostatic model as well as theoretical calculations may be used to simulate the electric field as well as particles distribution on the coating substrate which vary from the embodiments disclosed. EPD is acutely controlled by the electric field lines, which are dependent on the geometry and the placement of the electrodes. In order to realize the mass and the deposition morphology of the ceria NPs as they are being deposited on Ti implant surface to form the NC coating, the current distribution is modeled using an electrochemistry module in COMSOL software.

Figure 11A:
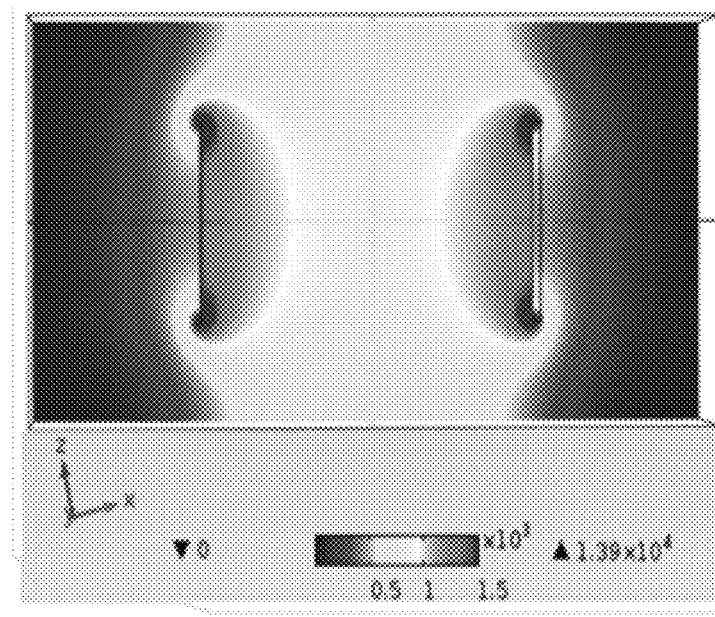
FIG. 11A shows the intensity of the electric field of the electrodes obtained by finite element modeling using COMSOL.
Figure 11B:
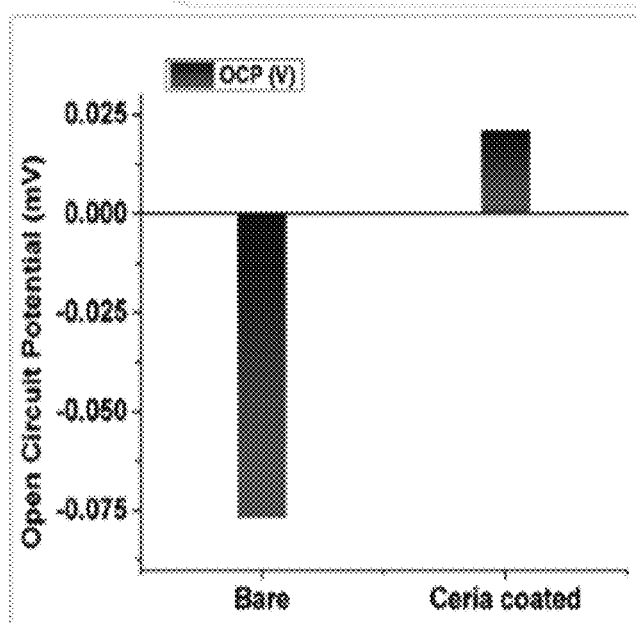
FIG. 11B shows the open circuit potential (OCP) of uncoated and NC coated sample substrates.

FIG. 11(A) shows the intensity of the electric field of the electrodes obtained by finite element modeling using COMSOL. FIG. 11B shows the open circuit potential (OCP) of uncoated (bare) and ceria coated samples obtained using an electrochemical test indicating a shift of potential from negative to positive. FIG. 11A shows the electrical field distribution on the surface of the electrode, which is directly proportional to the amount of NC deposition. The electric field numbers in the Figure use electric filed units of N/C. A 3-D geometry consisting of two sheet electrodes of dimensions 1"x1" separated by a distance of 5 mm was discretized using finite element mesh consisting of triangular elements having a highest size of 20 µm. The Ti electrode was grounded and a 60 V DC potential is applied between the electrodes. The ionic mobilities of CNPs (present in a dispersion suitable for EPD) as calculated from the zetasizer are assigned to the nanoparticles to obtain the ionic current distribution. The charge integration over the deposition time period shows the uniformity of the coating and the CNPs mass deposited. On the other hand, coating thickness will be very important for the anti-inflammatory property. According to one embodiment, a thin coating (of NC) (200-500 nm) is preferable, as probabilities of NC coated debris formation will be high rather than separate NC debris formation. Moreover, internal stress of the coating for thickness in the range of 200-500 nm will be limited to a certain extent and wear debris would be coated with the NC coating rather than uncoated debris. NC presence on the surface of the debris is preferable to, for instance uncoated Ti, because the NC coating suppresses the cascade of reactions responsible for inducing periprosthetic osteolysis.

Equation (1) is used to predict the coating thickness, where $w_0$ is starting weight of the solid particles in the solution, $\mu_e$ electrophoretic mobility, V, volume and $\rho$, suspension resistivity, E the applied direct-current voltage, and $\Delta E$ the voltage drop across the deposited layer. Electrophoretic mobility can be obtained using DLS measurement and $\Delta E$ is negligible voltage operating in this study (<100 V), therefore this equation may be used to predict the relationship between the time and thickness for a given voltage. It has been shown that <100 V and short deposition time (180 s), the thickness growth is proportional to time. Therefore, the electrodeposition process may occur over a range of time intervals to result in the thickness desired. After coating, substrates may be heated ~250° C. for 2 hr for better adhesion. The heating step may also be performed temperatures near 250 degrees and for a range of time. For instance, this step may also be heating the substrate to 200-450° C. for 1-2.5 hr.

Direct current and pulse EPD is shown in the FIG. 2A. Nanostructures are retained on both types of NC coatings. It is clear from the scanning electron microscopy that pulse EPD resulted in a more even coating compared to direct current EPD. In addition to EPD or pulse EPD, dip coating may be used in certain embodiments. For example, dip coating is used for glass cover slips and Ti-particles (<0.1 µm and <1 µm), and electrophoretic deposition (EPD) to coat the implant grade Ti & CoCrMo. Substrates disclosed are not limited to metal substrates, but also could be glass, which may be dip coated. Coated cover slips are used for confocal microscopy and catalytic measurement for ease of handling. This type of coating has application to particles coatings. It has been shown that debris generated for Ti are less than 10 µm and sometimes sub-nm, therefore <0.1 µm and <1 µm Ti particles will be selected for coating. After dip coating (varying parameters: concentration of CNP, pH and number of dips), samples will be heated at >450° C. for 2 hr in argon-purged atmosphere for better coating adherence. EPD parameters (electric field, pH and time will be varied to optimize the coating thickness, topology and chemistry of the coating. Similar heating steps will be followed as mentioned above. Variations include applying a voltage having a DC component and/or pulse to the substrate, having one or more counter-electrodes, or where the voltage is continuous (5 to 10 V), pulsed (1 sec pulse and 1 sec off for 20 cycles), or arbitrarily increasing or decreasing with time (30 to 60 sec).

Characterization of the Coating

For ease of reference, the term "CNP" as used herein refers to cerium oxide nanoparticles in particle form. Once the CNP's have been synthesized and deposited on a substrate, they are nanoceria (NC) coatings and no longer in particle form. The term "NC" shall refer to nanoceria generally.

The properties of these coatings have been determined. Topology and surface roughness are analyzed using both scanning electron microscopy (SEM) and atomic force microscopy (AFM). SEM provides over all surface morphology and porosity of the coating, where as surface roughness data is generated using AFM. AFM data is correlated to the cell culture and cell attachment behavior.

Figure 4:
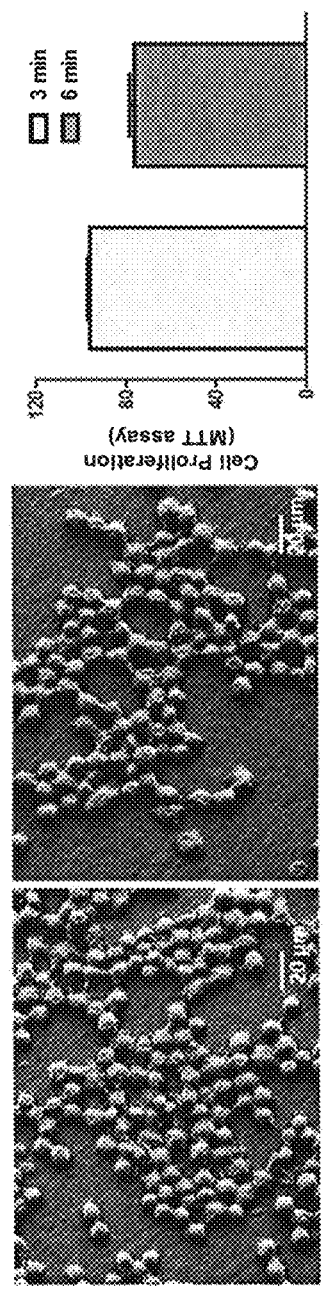
FIG. 4 depicts RAW cells grown for 18 hr on the surface of 3 min and 6 min EPD coated Ti substrate.

The topology and surface roughness may be analyzed using both scanning electron microscopy (SEM) and atomic force microscopy (AMF). FIG. 4 shows the different surface characteristics of two coatings manufactured using EPD coating. Coatings subjected to deposition for a longer time (6 minutes) as compared to 3 minutes had higher roughness and less attachment to RAW cells. (RAW cells were used in this instance as model cells to model cell attachment generally). Table 2 shows surface roughness at different coating times. A roughness of ~30-35 nm EPD coating was found to result in favorable cell attachment.

TABLE 1

Surface roughness of the coating measured using AFM

| Sample Description Ceria Coated Ti | Average Roughness- EPD coating only | RMS-EPD Coating only |
|---|---|---|
| AFM of Uncoated Ti Polished with 1000 Grit | 42 +/− 1 nm | 54 +/− 2 nm |
| AFM of 3 Minutes of EPD on Ti Substrate | 34 +/− 1 nm | 47 +/− 2 nm |
| AFM of 6 minutes of EPD on Ti Substrate | 43 +/− 7 nm | 63 +/− 16 nm |
| AFM of 12 minutes EPD on Ti substrate | 63 +/− 8 nm | 82 +/− 13 nm |

Figure 9:
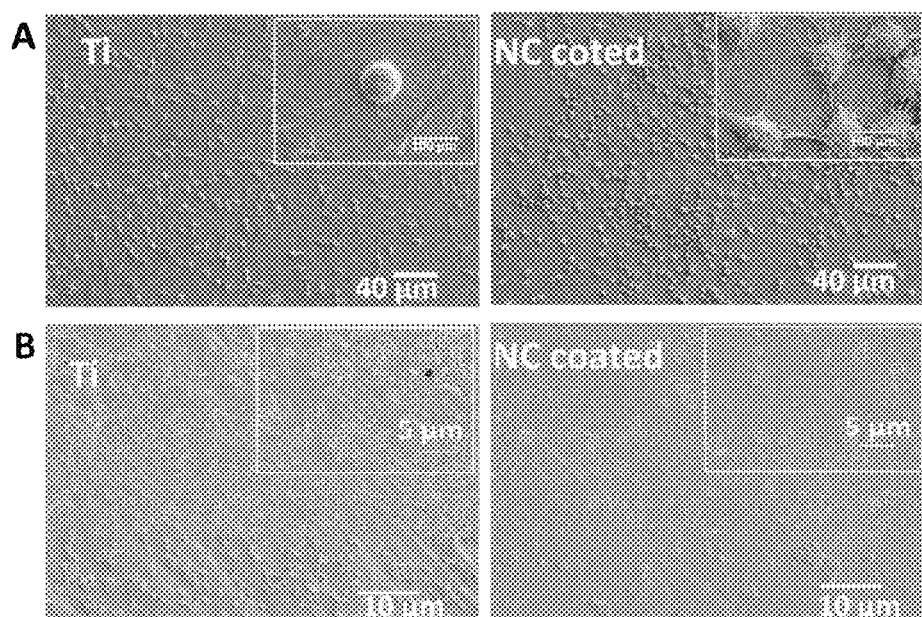
FIG. 9 are photos showing a comparison showing RAW cell growth on EPD coated Ti-substrate and a control Ti (uncoated).

FIG. 9 shows that EPD coated Ti-substrate are comparable to RAW cell growth as control Ti (uncoated), however an added unexpected benefit was that the growth of *S. aureus* was reduced (85%) (FIG. 9), a remarkable finding. Therefore substrates matching the surface profile of uncoated titanium metal are appropriate for embodiments.

The surface roughness of coatings is characterized using a number of other surface roughness parameters, such as Rq (Root Mean Square roughness), Rv (Maximum Profile Valley depth), Rp (Maximum Profile Peak Height), Rz (Average Maximum Height of the Profile), S (Mean Spacing of Local Peaks of the Profile, Sm (Mean Spacing of profile Irregularities, D (Peak Profile Density), or Pc (Peak Count).

An embodiment comprises a very thin coating of NC (200-500 nm) as probabilities of NC coated debris formation will be high rather than separate NC debris formation. Moreover, internal stress of the coating for thickness in the range of 200-500 nm is limited to a certain extent; and wear debris from a coated article (eg. a coated implant component) would be coated with ceramic coating. NC coating presence on the surface of the debris suppresses the cascade of reactions which induce periprosthetic osteolysis, and therefore disadvantages due to mechanical wear/debirs formation are reduced. Pulse electrophoretic deposition (EPD) of the NC coating provides a homogeneous coating on the substrate with better catalytic activity due to minimum alteration of the surface $Ce^{3+}/Ce^{4+}$ ratio of NC. It was found that a uniform coating of the substrate allows better cell attachment and growth. This was shown by coating NC on Ti substrate using pulse EPD (left) and EPD (right) using NC (FIG. 2A). The pulse EPD NC coating that ensures such cell attachment is achieved using following parameters 0.5 V-5 V, concentration of nanoparticles between 5-10 mM and 1 second pulse for 20-40 second in ethanol using NC surface charge of 47 mV and average particles size of 10 nm. The average surface roughness of the coating is at least in the range of 30-40 nm in an embodiment. The component may also be coated with one NC coating or multiple NC coatings having varying surface roughness.

Figure 6:
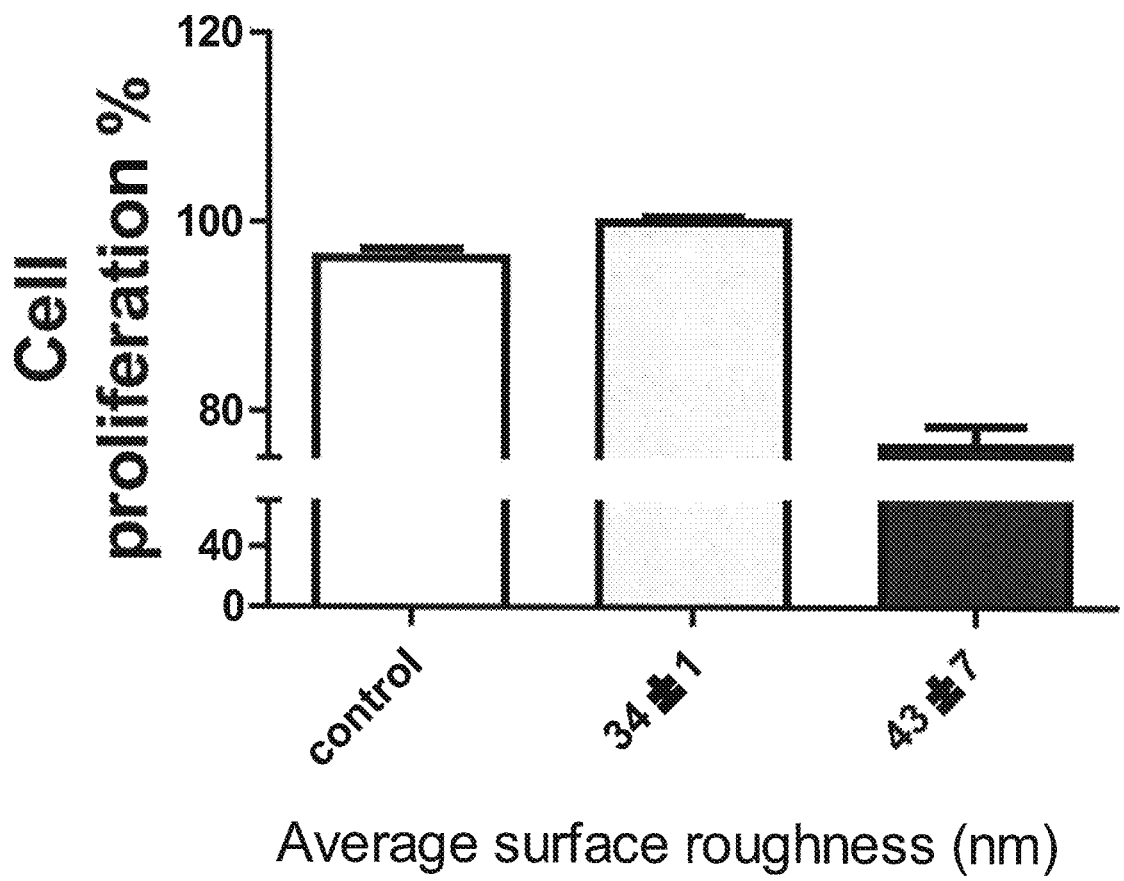
FIG. 6 shows a measure of cell proliferation on a coated Ti-metal substrate at different roughnesses, in accordance with an embodiment.

A range of thicknesses have been identified which do not interfere with cell attachment or proliferation. Cell proliferation and surface roughness is shown in FIG. 6, which shows the correlation with surface roughness with cell proliferation. For the test in FIG. 6, macrophage cells were used as a model for any cells in order to show general cell attachment. As mentioned previously, beneficial effects of the NC coating is a result of both the inducement of cell attachment and also a reduction of inflammation, such as when cells are challenged with LPS, for example. In order to obtain coatings of the range of thickness mentioned previously, a cross-section of the coating material may be analyzed using SEM to estimate the coating thickness, interface and the coating integrity. XPS may be carried out to analyze the surface chemistry of the coating to confirm catalytic property. Note crystallinity and wettability of the coating may be analyzed using XRD and contact angle analysis to correlate the cell attachment and biocompatibility. Scratch testing may also be used to estimate the adhesion strength of the coating for biomedical application in accordance with ASTM C1624 standard. Bio-compatibility of the material will be analyzed by seeding RAW cells on the substrate with and without coating. Cell density and viability of cell will be analyzed (24, 48 and 72 hrs) using fluorescence based LIVE/DEAD® Cell Viability Assays. Attachment of the cells will be determined as discussed elsewhere to understand the cell substrate interaction Cell attachment and proliferation of the RAW cells was found to be inversely proportional with increasing roughness of the coating, as shown in FIG. 6. It should be clarified here that in this Figure, the RAW cells growth and attachment were used to model general cell attachment and not, in this part of the study, to show a particular anti-inflammatory property. Anti-inflammatory properties were shown and described elsewhere in this disclosure. As mentioned previously, the beneficial effects of the NC coating is a result of the cell attachment generally and also its ability to reduce inflammation (inflammation for example being ROS or RNS or other reactive species in a cascade of processes earlier described). A substrate with minimum/no alteration of cell proliferation was determined based on the MTT data and used for ROS, RNS and NFkB-LUC experiment. No significant changes in ROS or RNS were observed in the presence of the coating as compared with a control substrate in the absence of stimulation with LPS or LPS PMA. A significant reduction in intracellular ROS and RNS were observed in the presence of the coating when challenged with LPS for ROS or LPS+PMA for RNS. NFkB-LUC activity was also significantly reduced in presence of coating in samples challenged with LPS.

Coating integrity: To estimate the coating thickness, a cross-section of the coating material is analyzed using SEM, interface evaluation and the coating integrity. The adhesion strength of the coating with substrate is evaluated using ASTM C1624 standard. The load may be varied linearly from zero to 40N for 10 mm scratch length. In that case, loading rate may be varied from 1ON/min to 100N/min based on maximum applied load. These variations are used to provide the critical load for coating failure. To access the failure mode, scanning electron microscopy (SEM) and surface profilometry will be performed along the scratch distance. The critical scratch load to determine a good coating is calculated from Equation (2): $L_{CN}=[L_{rate}\cdot(I_N/X_{rate})]+L_{start}$, Where, $L_{CN}$, $L_{rate}$, $I_N$, $X_{rate}$ and $L_{start}$ are critical scratch load (Newton) for a defined type of damage (N=number sequence), rate of force application (N/min), distance in mm between start of the scratch track and the start point of the particular type of damage in the scratch track, rate of horizontal displacement (mm/min), and pre-load stylus force (Newton) at the start of the scratch test.

Tangential force to normal force ratio at a specific point in the scratch test is called stylus drag coefficient (DSC) is calculated from Equation (3): $D_{SC}=L_T/L_N$ where $D_{SC}$, $L_T$ and $L_N$ are stylus drag coefficient, tangential force in the scratch test at a given point, and normal stylus force in the scratch test at a given point. For this ceramic coating, literature reported $D_{SC}$ values are in the range of 0.2-04[26].

Coating Chemistry and Compatibility

The surface chemistry of coatings synthesized can be altered by the medium (ethanol), electric field and heating. Cold stage XPS are carried out to analyze the surface chemistry as well as any impurity of the coating and correlated to the catalytic property. Crystallinity of the NC coating can also influence cell surface interaction. Therefore, crystallinity is analyzed using XRD and correlated with in vitro cell attachment and proliferation. Wettability and cell growth are highly dependent on each other. First, water molecules and small protein molecules are adsorbed on the implant surface. Larger proteins later replace these small proteins during second step. This protein adsorption step is influenced by wetting behavior of implant. Therefore, wettability of the coating is analyzed using contact angle analysis to correlate the cell attachment and biocompatibility. It is reported in the literature that moderate wetting (hydrophilic) shows better cell adhesion, cell growth and biocompatibility. More hydrophilic implant surfaces decrease cell adhesion. Therefore, protein moderate wetting is considered optimum for cell growth, adhesion and differentiation[27].

Corrosion behavior of coated Ti-plate is tested electrochemically and compared with control Ti.[28]. Application of ceramic coatings reduces the corrosion current ($I_{corr}$) and increases the open circuit potential ($E_{DC}$) to high value (see FIG. 11B), thus less current is allowed to pass through the cross section. The application of cerium oxide coating for anti-corrosion has also been reported[29]. Its anti-corrosion behavior has been tested on various metallic substrates such as stainless steel[29, 30], galvanized steel[31], aluminum alloy[32], magnesium alloy[33]. Preliminary data of the open circuit potential (OCP) shows a positive increase in case of NC coated Ti-substrate which indicate that NC coating prevents Ti-ion desolution in simulated body fluid (FIG. 11B). The corrosion test will include measurement of polarization resistance (Tafel curve) in a simulated body fluid. Corrosion studies in simulated body fluid (SBF) are carried out to mimic the body environment. Several Mg based biodegradable alloys, Ti and bulk metallic glass have been tested in SBF for corrosion behavior[435]. Different ions present in SBF develop galvanic cells and their reactivity depends on their presence in the EMF series. Corrosion behavior of implant in SBF simulates the body environment and demonstrates the combined effect of ions present in EMF series at different positions. Electrochemical impedance spectroscopy is recorded to further verify the corrosion resistance.

An NC coated substrate with different physical and chemical parameters is developed for a range of catalytic activity and compatibility screening. For successful EPD coating, the NPs should be positively charged, thus allowing deposition on a negatively polarized coating electrode. If surface charge of NC is negative/or near neutral, acid treatment will be used to modify the surface charge of the NC for better coating. Control coating of Ti-particles with NC using EPD could pose some challenges due to low yield as only a thin monolayer of Ti-Particles could be coated at a time. Moreover, some EPD techniques can produce only one side coating and may also have some free NC. Atomic layer deposition (ALD) is an alternative technique,[36] which can be used for Ti particles coating. ALD coatings builds on layer-by-layer deposition thus high precision thickness control is achievable. An objective is mainly to provide a novel anti-inflammatory coating which scavenges local free radicals and suppresses the immune reaction causing osteolysis.

Catalytic Activity

The inventors have previously shown NC with higher levels of cerium in the +3 oxidation state exhibit superoxide dismutase activity[37] and that this reactivity correlates with the level of cerium in the +3 oxidation state in a reversible manner[38]. Likewise, NC with higher levels of cerium in the +4 oxidation state exhibit better catalase mimetic activity[39] that also is reduced when higher levels of cerium are present in the +3 oxidation state. The inventors also present data on the reactivity of NC with two ROS, nitric oxide (NO) radical and the powerful oxidant peroxynitrite (ONOO—). Thus NC coatings have retained their catalytic properties that impart their core anti-inflammatory nature.

The reactivity of coated substrates with four primary molecules: 1) superoxide anion radical, 2.) Hydrogen peroxide, 3.) Nitric oxide radical and 4.) Peroxynitrite are determined. As mentioned previously, a difference is that the NC coating will be on a solid substrate and not in nanoparticle form. For this reason, known methods are modified to accommodate this distinction.

First, superoxide dismutase activity is detected using a standard 1 mL quartz cuvette so that a small piece of the coated material (on glass substrate or titanium substrate or particles) will be placed directly in the bottom of the quartz cuvette so as to not block the standard light path of the cuvette. This will be a general strategy that we will use to determine the reactivity with the aforementioned ROS and RNS. For each reactive molecule the general scheme for assay is described below:

(A) Superoxide radical anion. Superoxide is a short-lived radical that can only be detected by indirect means in vitro. A primary assay for determination of reactivity of the coated materials is using an assay that has been described multiple times in our previous studies competition between the reaction of superoxide generated from hypoxanthine/xanthine oxidase as previously described[37]. This assay measures the competition between the reaction of superoxide with ferricytochrome C and the material tested. This is an established assay for this reactive radical anion and has reliably correlated with other assays for cerium oxide nanoparticles. An alternative to this assay is to carry out electron paramagnetic resonance studies using spin traps as previously described[38].

(B) Hydrogen peroxide. The reactivity of cerium oxide materials with hydrogen peroxide has been appropriately described as catalase mimetic activity. There are a variety of methods that are used to detect the level of peroxides, including hydrogen peroxide, via spectrophotometric means. To assess the reactivity of material coatings, use a straightforward UV-visible assay using a 1 mL quartz cuvette[39]. The present inventors already determined that NC that is dip coated on glass retains its catalase mimetic activity using this approach (FIG. 2B). This not only shows that the assay can be used for this material, and for coated materials, but also indicates the core reactivity of cerium oxide with hydrogen peroxide is not lost during coating. An alternative to direct UV-visible assay for peroxide is to use Amplex Red dye that reacts with peroxide to give a resorfurin product that can also be detected by UV-visible spectrometry—albeit with a high extinction coefficient[39].

(C) Nitric oxide. For detection of changes in nitric oxide radical in the presence of NC coated materials, the approach described previously[40] may be used. Briefly, nitric oxide can be generated by a variety of approaches both chemical and biological. The use of so-called NONOates is most common, and most effective to generate a continuous stream of NO for reaction. S-nitroso-N-acetylpenicillamine (SNAP) is used to generate NO on a continuous basis in a standard reaction. This is followed by the conversion of ferrous hemoglobin to ferric hemoglobin by following changes in absorbance at 421 nm[40]. As an alternative, the concentration of NO in the presence and absence of coated materials in the presence of a copper-fluorescein conjugate may be tracked as previously described[40]. This conjugate reacts specifically with NO and generates a fluorescent product (excitation 503 nm, emission 530 nm) that directly correlates with NO levels. Using both of these methods confirms the reactivity of the cerium oxide coated materials (D) Peroxynitrite. Peroxynitrite is likely the most oxidizing biological RNS, and its production during inflammation is likely the most damaging aspect of this response. However it is very reactive and its breakdown yields a large number of products that include radicals, peroxides and short-lived intermediates. In order to determine reactivity of cerium oxide coated materials, the concentration of peroxynitrite is measured as opposed to any downstream products given the difficulty in interpreting this data. The decay of peroxynitrite is measured by UV visible absorption in the presence or absence of cerium oxide coated materials[41]. The present inventors have previously followed the reaction of cerium oxide nanomaterials with peroxynitrite, and found that cerium oxide accelerated the decay of peroxynitrite much in the same way that known scavengers do (uric acid for example).

To evaluate if coating retains the radical scavenging activity for quality control of the produced coatings, in situ degradation of $H_2O_2$ is analyzed. UV-Vis spectroscopy clearly indicates NC coating was able to scavenge $H_2O_2$ (FIG. 2B). FIG. 2B shows real time degradation of $H_2O_2$ followed absorbance at 240 nm. If substrates are coated with mixtures of NC that contain both types of particles (3+ higher SOD activity and 4+ peroxide & NO activity), the full range of catalytic activities are present.

Next, RAW 264.7 macrophage were grown on cover slips with or without NC coating and were stimulated with 5 μg/ml lipopolysaccharide (LPS) for 4 hr and intracellular reactive oxygen species (ROS; mainly $H_2O_2$) were measured using 2',7'-dichlorodihydrofluorescein diacetate ($H_2$DCFDA) described elsewhere[21]. Cells grown on the NC coating showed significant less ROS/$H_2O_2$ as compared to control (FIG. 2C). FIG. 2C shows ROS estimated using $H_2$DCF fluorescence in NC coated substrate.

Similarly, the level of intracellular reactive nitrogen species (RNS) was also measured using aminophenyl fluorescein (APF) after stimulation with LPS (5 μg/ml) and Phorbol 12-myristate 13-acetate (PMA; 1 μg/ml) as described elsewhere[22]. Significant reduction of RNS was observed in NC coating as compared to the uncoated ones; FIG. 2D shows RNS using APF fluorescence assay in NC coated substrate.

Anti-Inflammatory Properties Using a Macrophage Cell Culture Model System

Evaluation of coated materials as anti-inflammatory use a macrophage cell culture model system in an embodiment. A large number of studies have demonstrated that cerium oxide nanoparticles exhibit catalytic properties in cell culture model systems (reviewed recently in[42]). In vivo animal studies have shown that cerium oxide nanoparticles can display anti-inflammatory properties, presumably based on the catalytic reactions with ROS and RNS[43-49]. However it was neither previously known nor obvious as to whether this catalytic potential would be preserved following deposition to various base materials.

To determine the catalytic potential for each coating with pure ROS and RNS, there are two related goals 1.) To determine the ability of RAW cells to bind and adhere to NC coatings in vitro and 2.) To determine whether NC coatings can reduce inflammatory responses generated from activated RAW macrophages in vitro. This stimulation triggers a classic respiratory burst of ROS and RNS allowing for the determination of the level of several oxidants using both live cell imaging and confocal microscopy,[21, 22]. The response to M-CSF/CSF1 (33 ng/mL) and RANKL (66 ng/ml) in the same cell model is also measured as an alternative method for activation that is relevant to in vivo processes in osteolysis.

RAW 264.7 macrophage are grown on cover slips with or without NC coating and were stimulated with 5 μg/ml lipopolysaccharide (LPS) for 4 hr and intracellular reactive oxygen species (ROS; mainly $H_2O_2$) are measured using 2',7'-dichlorodihydrofluorescein diacetate ($H_2$DCFDA) described elsewhere. Cells grown on the NC coating showed significant less ROS/$H_2O_2$ as compared to control (FIG. 2C). Similarly, the level of intracellular reactive nitrogen species (RNS) was also measured using aminophenyl fluorescein (APF) after stimulation with LPS (5 μg/ml) and Phorbol 12-myristate 13-acetate (PMA; 1 μg/ml). Significant reduction of RNS was observed in NC coating as compared to uncoated (FIG. 2D).

Binding and Adhesion of RAW Cells to NC Coatings.

RAW cells are seeded onto NC coatings in 6-well dishes in Dulbecco's Modified Eagle's Medium with 10% fetal bovine serum. A seeding density of approximately 10% by area is used to study adherence and proliferation properties. Cells are cultured for 1-3 days and two sets of MTT assay are carried out. A.) to measure MTT reduction in the entire well or B.) to remove the NC coating materials (with sterile forceps) and place them into an empty well with only culture medium and subsequently add MTT to measure only adherent cells. These experiments serve as a quantitative measure of RAW cell binding to the NC coating. Controls (no NC coating on base metal/glass substrate) and empty wells to differentiate background binding within the cell population are naturally employed.

Anti-Inflammatory Activity Exhibited by NC Coatings on Activated RAW Cells.

Figure 10:
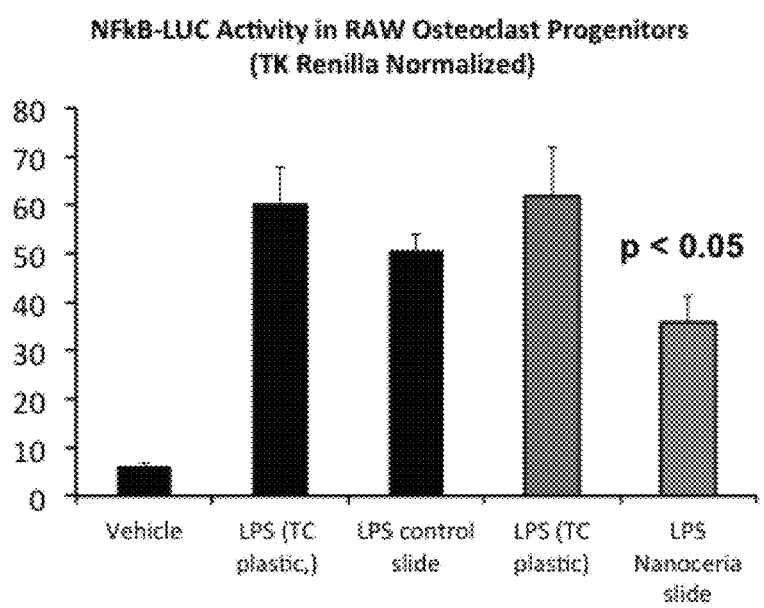
FIG. 10 is a graph showing NFkB-LUC Activity in RAW osteoclast progenitors (TK Renilla Normalized).

In parallel plate, RAW cells at 10% confluence are allowed to interact with either the NC coatings or control substrates overnight. After 24 the RAW cells are stimulated with either M-CSF/CSF1 (33 ng/mL) and RANKL (66 ng/ml), LPS (5 μg/mL), or LPS (5 μg/mL) along with phorbol 12-myristate 13-acetate (PMA) (1 μg/mL). Intracellular ROS is then measured using Intracellular ROS using 2',7'-dichlorodihydrofluorescein diacetate ($H_2$DCFDA) as previously described in our work[21, 50]. This probe is considered a general probe for ROS and likely correlates best with steady state hydrogen peroxide levels. To determine changes in RNS level the aminophenyl fluorescein (APF) is used that has been shown to correlate better with changes in the level of RNS[50]. In parallel, RAW264.7 cells are transfected with the NFkB-LUC reporter and the impact of NC coatings on LPS, LPS+PMA, or MCSF/CSF1+RANKL reporter activity to assess impact on NFkB signaling in vitro is assessed (see FIG. 10).

It previously has been described and utilized various methods to detect changes in the level of reactive oxygen or nitrogen species (ROS or RNS). NC coatings that have good catalytic activity will reduce the levels of ROS and/or RNS in activated macrophages (RAW cells) and NFkB signal activation. NC coatings that retain high levels of cerium in the +3 oxidation state will exhibit superoxide dismutase activity. Likewise for NC coatings that have higher levels of cerium in the +4 oxidation state at the surface a higher reactivity with peroxide (catalase mimetic activity) and NO is observed. Finally the decay of peroxynitrite may be accelerated by either material coating.

Coatings with mixtures of NC (NC 1 and NC2) exhibit a full range of catalytic activities. Alternate approaches to both coating the substrate and testing the reactivity are other possible scenarios, and it has been shown that several methods can be applied in observing the catalytic reactivity with ROS and RNS[10, 21, 37-39, 46, 50]. For example electron spin resonance spin traps (DEPMPO) may be used to determine whether these materials are directly reducing the level of superoxide radicals or hydroxyl radicals. These are not selected as primary methods since measuring kinetics using ESR is more difficult, but nonetheless we there are other options to measure ROS and RNS in the presence of these coatings.

Other embodiments include methods for assembling ceria nanoparticles on the surface of Ti (and other metal alloys, such as CoCrMo) such that a NC coating is formed to retain the ROS/RSN catalytic properties that convey anti-inflammatory properties. The presence of NC in the milieu of the prosthetic-bone interface will enhance osseous integration. This is shown via studies of the impact of nanoceria-coated titanium on NFkB-dependent osteoclast differentiation, activation, and bone resorption, using RANKL-stimulated human osteoclast progenitors and bone resorption as a model for study.

Impact of Nanoceria-Coated Implant Material on (a) Osteoclast Differentiation and Activation, and (b) Osteoblast-Mediated Matrix Mineralization, Using Commercially Available Primary Human Osteoclast Progenitors and Human Osteoblasts in Culture as Models for Study.

The skeletal response to wear debris frequently results in an inflammatory periprosthetic osteolysis. The cell types responsible for bone resorption and loosening in this setting arise from the monocyte/macrophage lineage—primarily an inflammatory osteoclast ("OC"). The Rel domain transcription factors NFkB and NFATc1 play particularly important roles downstream of RANKL/TNFSF11 stimulation, a key member of the TNF superfamily whose tone directs OC lineage allocation and activity via NFkB and NFATc1. Classical and alternative activation pathways entrain nuclear localization of NFkB, with ROS principally $H_2O_2$ amplifying and propagating NFkB activation downstream of LPS and TNF superfamily members in multiple cell types. Novack and colleagues recently demonstrated that activation NIK—a unique component of the alternative NFkB pathway activated by RANKL—was key in development of the inflammatory OC, confirming the importance of this pathway.

Whether NC will modulate ROS-dependent amplification of the RANKL/NIK (NFkB inducing kinase)/NFkB signaling pathway—and thereby mitigate inflammatory osteoclast differentiation and activity in vitro is assessed. Because bone-forming osteoblasts exhibit limited synthetic responses under states of inflammation and oxidative stress, the impact of optimized nanoceria coatings on human osteoblast mineralize matrix formation and osteogenic differentiation are determined.

Bone resorption by OCs requires secretion of cathepsin K (catK), a panoply of MMPs (MMP9, MMP14), and protons in resorption pits to degrade collagen and mobilize calcium and matrix factors including TGF-beta1. Basal osteoclast activity helps sustain the healing angiogenic response and robust osteoprogenitor recruitment in part via MMP9, Wnt ligands, and chemokines. However, excessive ROS reduces osteoblast mitochondrial membrane potential, synthetic activity, and increase RANKL production and osteoclast activation. Thus, strategies that mitigate an excessive oxidative inflammatory response by osteoblasts and osteoclasts lead to improved osseous integration, including MMP9 and MMP14 (MT1-MMP) to degrade collagen and enable cell migration. Additionally, resorption pit acidification by V-ATPase is critical to both zymogen activity and calcium mobilization.

Figure 5:
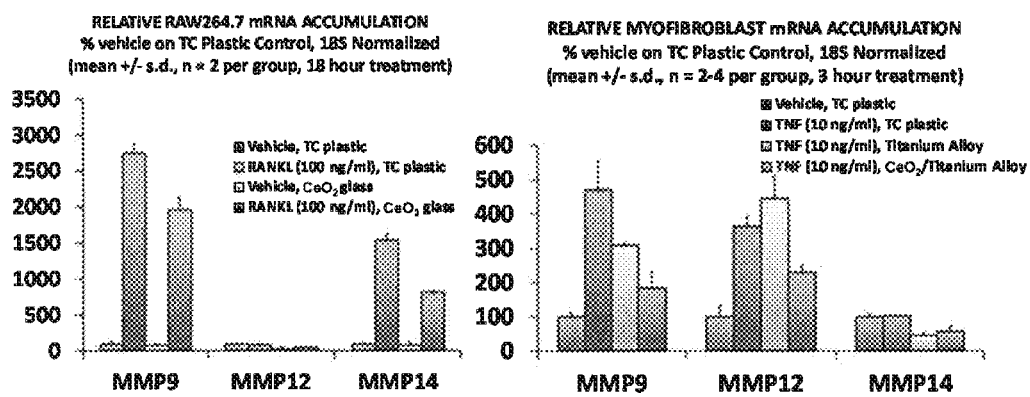
FIG. 5 shows matrix metalloproteinases, MMP9, MMP12 and MMP14 expression in a nanoceria coated substrate after induction with RANKL OR TNF.

To address whether NC-coated surfaces mitigate programmed inflammatory responses, RAW264.7 murine osteoclast progenitors were plated along with primary vascular (adventitial) myofibroblasts on NC-coated titanium or glass surfaces. As shown in FIG. 5, left panel, RANKL induction of MMP9 and MMP14 was reduced when RAW264.7 cells were plated on NC coated glass. Furthermore, activation of NFkB-LUC by LPS was significantly reduced by 42% on NC-coated glass vs. uncoated glass or plastic (p=0.04, n=6/group). Similarly, when cultured on plastic or titanium TNF upregulated myofibroblast expression of multiple metalloproteinases including MMP9, MMP12, and MMP13. However, NC-coated titanium surfaces reduced MMP9, MMP12, and MMP13 expression even in the presence of TNF (FIG. 5, right panel).

Figure 7:
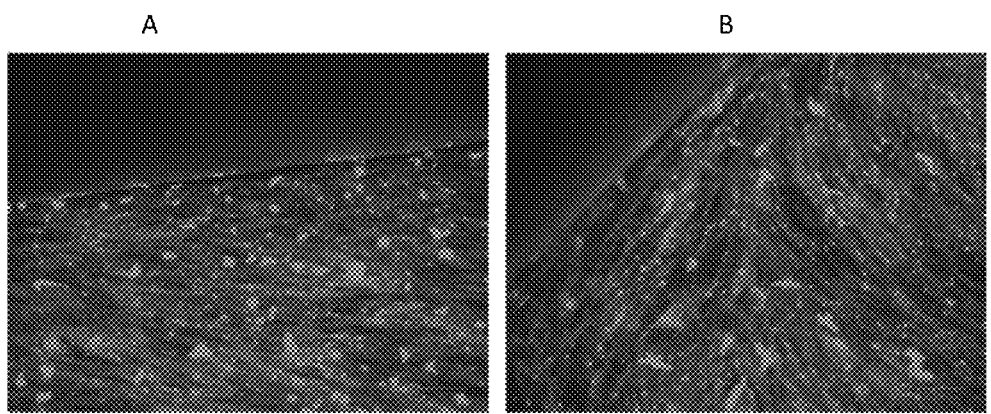
FIG. 7 shows primary han osteoblasts were plated onto type I collagen-coated (A) control or (B) NC-coated Ti plates & cultured for 8 days. Alkaline phosphatase activity was visualized by Vector Red staining, in accordance with an embodiment.

The data indicate that nanoceria coatings do not impair the early phases of Lonza NHOst primary human osteoblasts in culture (FIG. 7). FIG. 7 shows primary han osteoblasts were plated onto type I collagen-coated (A) control or (B) NC-coated Ti plates & cultured for 8 days. Alkaline phosphatase activity was visualized by Vector Red staining. As can be seen from comparing the images, no gross differences were observed, and no staining is observed on the uncoated sides.

Thus, the data shows that NC coatings reduce inflammatory osteoclast activation and bone resorption without impairing osteoblast synthetic functions as relevant to wear-debris responses in periprosthetic osteolysis. This may be further validated using human primary monocyte osteoclast progenitors (e.g. from Lonza (2T-110)). In this system, co-treatment with M-CSF/CSF1 (33 ng/mL) and RANKL (66 ng/ml) is required for 7-14 days to induce osteoclast differentiation of progenitors when cultured on OsteoAssay Human Bone Plates (Lonza PA-1000) or bone slices (IDS/Immunodiagnostics DT-1BON1000-96). Bone resorbing activity is quantified by measuring type I collagen telopeptide (CTX) released to the culture supernatants due to osteoclast actions on OsteoAssay Human Bone Plates. Key osteoclast differentiation markers (MMP9, CatK, TRAP, beta3 integrin, calcitonin receptor, DC-STAMP) are measured by RT-qPCR (Taqman Gene Expression Assay) using RNA extracted from cells cultured on OsteoAssay Human Bone. In parallel, Western blot analysis, zymography, and ELISAs are used to quantify oxidative pro-MMP9 activity, MMP9, and cathepsin K as pathophysiologically important markers of osteoclast function. Similarly, osteoclast activity on bone (or dentine) surfaces creates resorption pits that can be quantified by digital image analysis following staining with toluidine blue. Actin double ring sealing zone formation—sina qua non for true osteoclast activity—is assessable by FITC-phalloidin staining and epifluorescence imaging on bone disks as described by Novack et al.[88]

Briefly, in quadruplicate and in 96 well format, 10K (10,000) human osteoclast precursors are plated in 100 ul of OPBM Bullet Kit Basal Media containing either vehicle or 2×MCSF+RANKL onto either Lonza Human Bone Plates or IDS bone slice plates previously coated with 100 microliters of (a) control media (no microspheres); (b) media with <0.1 µm and <1 µm Titanium microspheres (American Elements); or (c) media with NC coated Ti-microspheres.

The <0.1 µm and <1 µm micron particle size is initially chosen since the mean size of particulate wear debris reported in failed knee and hip arthroplasty has been reported to be between 0.5 µm and 1 µm and is engaged by phagocytosis. The smaller 0.1 µm size is included since debris of this diameter is taken up by cells via fluid-phase pinocytosis. A dose-ranging of microsphere administration will initially encompass 1E5, 1E6, and 1E7 particles per well, for 10:1, 100:1, and 1000:1 ratios of particles per osteoclast progenitors plated. Additionally, as a positive control, co-treatment with 5 uM cardamonin—a previously validated pharmacological inhibitor of RANKL/NFkb signaling in the myeloid lineage—in OPBM Bullet Kit Basal Media+/−MCSF+RANKL will be used to establish the dynamic inhibition range possible via the NFkB-dependent program regulated by NC.

Following 7 days in culture, the supernatant is analyzed for human CTX-I by CrossLaps Elisa (For culture; IDS catalog number AC-07F1) and RNA extracted from monolayers (Qiagen RNeasy PLUS 96 Kit cat #74192) for analysis of human MMP9, MMP12, MMP14, Cathepsin K (major collagenase), Atp6v1c1 (osteoclast V-ATPASE proton pump, acidifies resorption pits), calcitonin receptor, beta3 integrin, DC-STAMP, and mRNAs normalized to 18S rRNA control.

Key proteins markers are evaluated as above. In parallel, cell plated as above onto bone slices are cultured for a total of 14 days. As before, culture supernatants are collected for CTX-I quantification by ELISA. Following washing with PBS and ultrasonication in 250 uL of 70% isopropanol, resorption pits are visualized by toluidine blue staining (100 µl of 1% TB for 3 minutes), rinsed in ddH$_2$O and digital images under light microscopy of the dark blue pits quantified by ImageJ software for both area and number. In a parallel, cells plated onto bone slices (vide supra) are cultured for a total of 7 days, supernatants harvested for CTX-I ELISA, and bone slice-associated osteoclasts fixed and stained with FITC-phalloidin, DAPI, and Alexa594-conjugated anti-p100/p52 (Cell Signaling RabMab clone 18D10) to image and quantify actin ring sealing zones, nuclei, and nuclear NFkB2 localization, respectively, following epifluorescent illumination.

Quantitative assessment of normal human osteoblast differentiation is also characterized as in rodent systems, assessing alkaline phosphatase activity, calcium deposition by alizarin red staining/solubilization/spectrophotometry, and osteogenic gene expression and RANKL by RT-qPCR. Osteoblast mitochondrial DNA damage will be quantified by multiplex Taqman assay quantifying % human mtDNA deletion and cellular respiration/mitochondrial function assess by trypsinizing and replating nanoceria-exposed osteoblast into collagen-coated XFp Seahorse Miniplate followed by Cell Mito Stress Testing using an XFp Flux Analyzer.

No deleterious actions of NC exposure have been observed with respect to osteoblast differentiation, proliferation or metabolic function—mineralization may in fact be increased due to reductions in accumulating ROS. Like cardamonin, Ti-microsphere coated with NC exhibits reduced RANKL-dependent osteoclast activity, reflected in reduced CTX-I release into culture media, reduced expression of NFkB-dependent transcripts, osteoclast pit resorption area, & decreased actin sealing zone area & nuclear NFkB2 accumulation. If pit number is not reduced, this indicates selective action on resorption and migration in setting of reduced resorption area. If reduced, it may indicate either decreased osteoclastogenesis and/or reduced osteoclast progenitor viability with loss of RANKU/NFkB signaling tone. Validated human cellular reagents are used and examples are provided to encompass differentiated primary murine bone mononuclear cells in addition to murine RAW264.7 cells to initiate implant studies in rodents since osseous integration of NC-coated material is examined in preclinical orthopedic models of healing and strength. Moreover, reporter mice expressing luciferase down-stream of NFkB and NFATc response elements exist that can help guide and "fine-tune" in vivo the transcriptional inflammatory response in addition to the specific types of cellular inflammatory foreign body responses elicited in bone to wear debris and as modified by NC coatings.

The impact of nanoceria-coated titanium on NFkB-dependent osteoclast differentiation, activation, and bone resorption, is assessed using RANKL-stimulated human osteoclast progenitors and bone as a model for study. The presence of optimized NC coating onto implant surfaces reduces the pro-inflammatory ROS/RNS signaling that promotes bone-resorbing osteoclast function—a primary cellular mediator of prosthetic implant loosening and impair osseous integration in ARMD osteolysis[11] driving TJR failure. As outlined, the skeletal response to wear debris frequently results in an inflammatory periprosthetic osteolysiss. The cell types responsible for bone resorption and loosening in this setting arise from the monocyte/macrophage lineage—primarily an inflammatory osteoclast (OC)—but mesenchymal cells (wound myofibroblasts, osteoblasts) also elaborate proteases and matrix constituents that impact integration (e.g., FIG. 5)[51]. FIG. 5: MMP9, MMP12 and MMP14 expression in ceria coated substrate after induction with RANKL OR TNF.

The Rel domain transcription factors NFkB and NFATc1 play particularly important roles downstream of RANKL/TNFSF11 stimulation, a key member of the TNF superfamily whose tone directs OC lineage allocation and activity via NFkB and NFATc1[11-13]. Classical and alternative activation pathways entrain nuclear localization of NFkB, with ROS principally H$_2$O$_2$ amplifying and propagating NFkB activation downstream of LPS and TNF superfamily members in multiple cell types[52-54]. Novack and colleagues recently demonstrated that activation NIK—a uniquely component of the alternative NFkB pathway activated by RANKL—was key in the development of the inflammatory OC, confirming the importance of this pathway[11]. Bone resorption by OCs requires expression and secretion of cathepsin K (catK) and panoply of MMPs including MMP9 and MMP14 (MT1-MMP) to degrade collagen and enable cell migration. Additionally, resorption pit acidification by V-ATPase is critical to both zymogen activity and calcium mobilization. Since human bone cells (osteoclasts, mesenchymal osteoprogenitors) represent the clinically relevant cell type whose behavior is the focus of the disclosed embodiments, the tests for the impact of NC-coated surfaces upon basal and RANKL-stimulated human osteoclast bone resorption is performed using the OsteoAssay Human Bone Plate from Lonzas.

Human primary monocyte osteoclast progenitors may be purchased from Lonza (2T-110). In this system, co-treatment with M-CSF/CSF1 (33 ng/mL) and RANKL (66 ng/ml) is required for 7-14 days to induce osteoclast differentiation of progenitors when cultured on OsteoAssay Human Bone Plates (Lonza PA-1000)[55] or bone/dentine slices[56] (IDS/Immunodiagnostics DT-1BON1000-96). Bone resorbing activity can be quantified by measuring type I collagen telopeptide (CTX) released to the culture supernatants due to osteoclast actions on OsteoAssay Human Bone Plates. Key osteoclast differentiation markers (MMP9, CatK, TRAP, beta3 integrin, calcitonin receptor, DC-STAMP) are measured by RT-qPCR (Taqman Gene Expression Assay) using RNA extracted from cells cultured on OsteoAssay Human Bone using the methods we've previously detailed[57-59]. Similarly, osteoclast activity on bone (or dentine) surfaces creates resorption pits that can be quantified by digital image analysis following staining with toluidine blue on IDS bone slices as described. Actin double ring sealing zone formation—sina qua non for true osteoclast activity—is assessable by FITC-phalloidin staining and epifluorescence imaging on bone disks as described by Novack et al.[12, 13] Briefly, in quadruplicate and in 96 well format, 10K (10,000) human osteoclast precursors will be plated in 100 ul of OPBM Bullet Kit Basal Media containing either vehicle or 2×MCSF+RANKL onto either Lonza Human Bone Plates or IDS bone slice plates previously coated with 100 microliters of (a) control media (no microspheres); (b) media with <0.1 μm Titanium microspheres; (c) media with <1 μm Titanium microspheres; (d) media with NC coated <0.1 μm Ti-microspheres; or (e) media with NC coated <1 μm Ti-microspheres. The <0.1 μm and <1 μm micron particle sizes are initially chosen since the mean size of particulate wear debris reported in failed knee and hip arthroplasty has been reported to be between 0.5 μm and 1 μm and is engaged by phagocytosis[60,61]. The smaller 0.1 μm size is included since debris of this diameter is taken up by cells via fluid-phase pinocytosis[62]. A dose-ranging of microsphere administration will initially encompass 1E5, 1E6, and 1E7 particles per well, for 10:1, 100:1, and 1000:1 ratios of particles per osteoclast progenitors plated. Additionally, as a positive control, co-treatment with 5 uM cardamonin—a previously validated pharmacological inhibitor of RANKU/NFkb signaling in the myeloid lineage[63]—in OPBM Bullet Kit Basal Media+/−MCSF+RANKL will be used to establish the dynamic inhibition range possible via the NFkB-dependent program regulated by NC. Following 7 days in culture, the supernatant will be analyzed for human CTX-I by Cross-Laps Elisa for bone resorption (For culture; IDS catalog number AC-07F1) and RNA extracted from monolayers (Qiagen RNeasy PLUS 96 Kit cat #74192) for RT-qPCR analysis of human osteoclast markers MMP9, MMP12, MMP14, Cathepsin K (major collagenase), Atp6v1c1 (osteoclast V-ATPASE proton pump, acidifies resorption pits), calcitonin receptor, beta3 integrin, DC-STAMP, and mRNAs normalized to 18S rRNA control. In parallel, cell plated as above onto bone slices will be cultured for a total of 14 days. As before, culture supernatants are collected for CTX-I quantitation by ELISA[64, 65]. Following washing with PBS and ultra sonication in 250 uL of 70% isopropanol, resorption pits are visualized by toluidine blue staining (100 μl of 1% TB for 3 minutes), rinsed in ddH$_2$O and digital images under light microscopy of the dark blue resorption pits quantified by digital image analysis with ImageJ software[66] for both area and number[11-13]. In a parallel, using techniques previously implemented[57-67], cells plated onto bone slices (vide supra) are cultured for a total of 7 days, supernatants harvested for CTX-I ELISA, and bone slice-associated osteoclasts fixed and stained with FITC-phalloidin, DAPI, and Alexa594-conjugated anti-p100/p52 (Cell Signaling RabMab clone 18D10) to image and quantify actin ring sealing zones, nuclei, and nuclear NFkB2 localization, respectively, following epifluorescent illumination (nuclear NFkB2:RelB complex key to RANKL osteoclast differentiation;[12, 13].

In parallel, normal human osteoblasts (Clonetics NHost; Lonza #CC-2538) are expanded then cultured in 12 well cluster plates (50,000 cell/cm2) on mineralization media (10% FBS, alphaMEM supplemented with 3 mM beta-glycerol phosphate+50 ug/ml ascorbic acid) in (a) the presence or absence of 5 ug/ml lipopolysaccharide (LPS) and (b) NC-coated vs. uncoated titanium microspheres at 0, 4E6, 4E7, and 4E8 spheres per well (corresponding to ca. 0, 10:1, 100:1, and 1000:1 spheres per osteoblast at confluence). All experimental sets are performed in quadruplicate, encompassing both <0.1 micron and <1 micron spheres. Cells are re-fed twice per week for 21 days, with fresh media and spheres added with each feeding following gentle rinsing in warmed media. At the end of the culture period, cultures are processed for quantification of calcification by Alizaran red staining we've previously detailed[57,58,67]. Conditioned media is collected at each refeeding and processed weekly for type I collagen propeptide measurement by ELISA (P1NP; bone formation and matrix synthesis marker[16]). Elaboration of the osteogenic gene regulatory program is quantified by RT-qPCR (initially querying bone alkaline phosphatase=akp2fNAP, bone sialoprotein, osteocalcin, Col1A1 and Col1A2 vs. Col2A1 and Col10A1, Runx2, Osx, Msx2, RANKL, OPG, MMP9, MMP12, MMP14/MTIMMP, TNF,) with normalization to 18S rRNA. In separate 24 well-culture format, human osteoblast/NHOST apoptosis will be assays using the Cayman Multiparameter Apoptosis Fluorescence Assay (#600330; 96 well capable but 24 well preferred re: plating), scoring LPS-induced apoptotic responses in the presence or absence of the NC-modified Ti microspheres dose-response. LPS treatment is chosen since this a (patho) physiologically relevant stimulus that conveys risk for failure of prosthetic osseous integration in vivo. Should significant differences exist between titanium and NC-coated titanium cultures with respect to osteogenic mineralization and/or P1NP/type I collagen synethesis, an exploratory analysis may be undertaken with UTSW Genomice and Microarray Facility implementing PrimeView Human Gene Expression Array (best reproducible coverage of the ANNOTATED human transcriptome) with RNA samples possessing RIN>=7 as done in our analyses of murine mineralizing tissues[57,58].

Based upon the data presented in the Figures herein, the Ti-microsphere coated with NC will exhibit reduced RANKL-dependent human osteoclast activity, reflected in reduced CTX-I release into culture media, reduced expression of NFkB-dependent transcripts (e.g., MMP9 and MMP14, potentially CatK, others), reduced osteoclast pit resorption area, & decreased actin sealing zone area & nuclear NFkB2 accumulation. Pit number may or may not be reduced. If pit number is not reduced, this indicates selective action on resorption and migration in setting of reduced resorption area. If reduced, it may indicate either decreased osteoclastogenesis and/or reduced osteoclast progenitor viability with loss of RANKU/NFkB signaling tone.

Furthermore, it follows that (a) human osteoblast (NHOST) mineralization will not be inhibited by exposure to NC-coated Ti-microsphere; and (b) osteogenic differentiation and mineralization are restored by NC-coated Ti microspheres in LPS-treated NHOST cultures. As in osteoclasts, targets of LPS-elicited NFkB signaling in osteoblasts (e.g., the above MMPs, TNF expression itself) and NHOST apoptosis are reduced by exposure to NC-coated Ti microspheres. Because titanium itself has been variably described as enhancing osteoblast synthetic function[68], it may be that NC-coating might diminish basal osteoblast activity but restore LPS-inhibited mineralization via its "catalase-like" activity. In this case, optimization of NC-coating mass/titanium surface area is iteratively pursued using methods described above and metrics of osteoblast function, to retain anti-inflammatory function while minimizing any potential basal advantage of titanium implant exposure.

Example: In Vivo Use of Coated Substrates

To assess how nanoceria coating of titanium impacts inflammation, net bone mass accrual, and skeletal tissue repair in vivo, diabetic mice are used as a model for study. Patients with type II diabetes (T2D) are particularly prone to lower extremity arthritis, fracture, and amputation in part due to the low-grade systemic inflammatory state of the disease, with concomitant neuropathy and vasculopathy[2, 4-7]. Preclinical models of dysmetabolic disorders such as diabetes, dyslipidemia, and chronic kidney disease recapitulate the pro-inflammatory states that impair fractions healing and osseous integration. Therefore, the model is implemented in a well-defined murine model of T2D and dyslipidemia—the male low density lipoprotein receptor null mouse (LDLR−/−) fed high fat diet[14-19]—to characterize the impact of nanoceria coatings on bone histomorphometric/histological response to titanium implant. Biomechanical strength and osseointegration of NC-coated Ti vs. uncoated Ti are thereby confirmed in vivo as well as supporting in vitro data.

Figure 12:
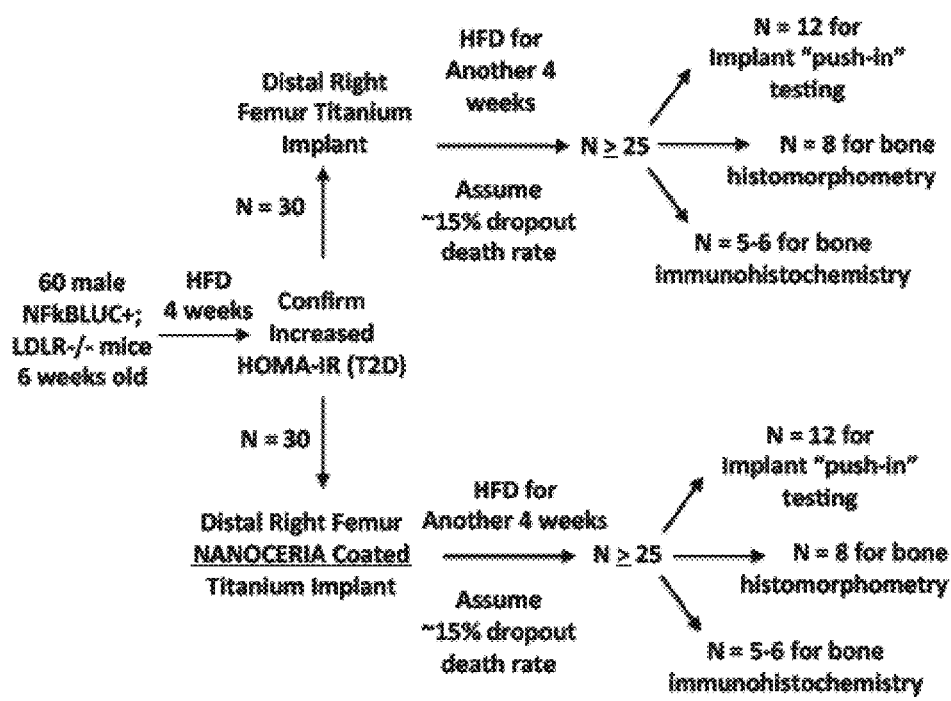
FIG. 12 shows a flow chart for in vivo testing to confirm anti-inflamatory properties, osseointegration, and mechanical testing of coatings, in accordance with embodiments.

Because inflammatory ROS/RNS signaling upregulates bone-resorbing osteoclast differentiation and monocyte/macrophage activities while suppressing osteoblast-mediated bone formation, the ROS/RNS catabolic activities of NC-coated titanium implants enhance healing and osseous integration around Ti prosthetics in vivo. Because the dysmetabolic state of T2D and metabolic syndrome impairs skeletal repair processes in vivo in both clinically relevant murine disease models[14-69] and in human patients[4-7], the NC coating is evaluated on osseous integration in the L DLR−/− mouse fed high fat diabetogenic diet[18, 57]. Since distal femurs implant model with "push in" mechanical testing has been recently established to evaluate ossseointegration in the setting of murine chronic kidney disease (CKD)[20, 70], the present inventors deploy this novel mechanical testing system that has emerged as more sensitive than pull out in preclinical assessments of osseous integration[71]. All animal data collection and presentation are in compliance with ARRIVE guidelines[72, 16, 57, 67, 73] To register NFkB signaling in vivo, NFKB-LUC reporter mice are utilized, B10.Cg-H2$^k$ Tg(NFkB/Fos-luc)26Rinc/J (stock #006100) using firefly luciferase IMMUNOHISTOCHEMSTRY[74]alongside nuclear NFKB2 histochemistry. Although in culture there is a nanoceria surface-dependent reduction in NFkB-driven transcriptional activity by luciferase assay following LPS stimulation (FIG. 10), the expression of skeletal tissue expression must encompass immunohistochemistry using the methods previously demonstrated[57,58,67]. To enable this, NFKB-LUC reporter mice are bred for 5 generations onto the LDLR−/− parental C57BL/6J background to enable diet-induced diabetes and dyslipidemia as others and we have previously described[18, 57, 75]. The line will be expanded and 100 male NFkBLUC; LDLR−/− male siblings challenged with high fat diet (Paigen formulation of the diabetogenic High Fat Diet[14, 18]) to induce diabetes, dyslipidemia, and bone disease (FIG. 12). After 4 weeks, animals will be fasted for 4 hours and retro orbital blood obtained under tribromomethanol anesthesia to confirm increased fasting blood glucose, insulin, and HOMA-IR as we've previously shown[57]. Once confirmed, the two days later the hair of the right lower extremity is shaved under anesthesia and using asepetic techniques, a unilateral distal right femoral lateral-to-medial submetaphyseal hole will be introduced orthogonal to the lateral aspect by sequential 0.7 mm and then 1.0 mm with a Dremmel hand drill and sterilized stainless steel bits—with normal saline irrigation for tissue cooling[20, 70]. A sterile 1 mm by 2 mm implant (NC-coated titanium vs. titanium, sterilized in 100% ethanol and dried, no UV sterilization to avoid potential confounding photofunctionalization) is placed in the femur by gentle tamping, and wound closed with 6-0 silk to secure overlying muscle and fascia, and 5-0 silk for skin closure. Two×0.4 cc normal saline (35 C warmed) subcutaneous fluid "boluses" administered (one over each flank) per mouse (one just before, one just after surgery) along with 0.05 mpk of subQ buprenorphine for pain control, and the mouse allowed to recover from surgery and anesthesia on a warming blanket with close post-operative monitoring.

The following day, high fat diet continues to be provided but now within the cage during recovery with water gel pack hydration and daily buprenorphine 0.05 mpk for three days. Our own experience with invasive surgery femoral surgery to date yields a ca. 10% perioperative mortality. Being more conservative, 15%=16% dropout rate is assumed, enabling at least 41 mice in each group to continue to experience HFD-induced diabetes, dyslipidemia, and bone disease for an additional 4 weeks. At the end of the dietary challenge, mice are fasted 4 hours with ad lib access to water then sacrificed by exsanguination under general anesthesia for harvest and analysis of femoral tissues as outlined below. Our personal histological assessment of bone and other mineralized tissues place the need for histology/histomorphometry at a minimum of 5 animals per group per replicate[58, 76-78]. Any additional animals will be tasked to histomorphometry given its variance[58, 76-78]. For push-in mechanical loading, 10 mice are included per arm based upon the recent published literature of Lanske and colleagues[20, 70].

Histomorphological assessment of bone implant contact interface and adjacent bone volume to tissue volume in non-decalcified plastic sections (n=5 per group). Non-decalcified bone plastic sections will be prepared essentially as we've previously described[58, 77, 78], but using a saw microtome as below. The distal ⅓ of the implanted femur is harvested, carefully cleared of adherent tissue and fixed en bloc overnight in 70% ethanol, dehydrated in graded acetone at 4C (70%×2 hrs, 90%×1 hours, 100%×2 hours).

Samples are sequentially infiltrated with 85% methylmethacrylate/15% dibutylphthalate/0.15% benzoyl peroxide in a 20 ml glass Wheaton vial a vacuum desiccator for 48 hours at 4C). Methacrylate polymerization[79] solution is then initiated at 37C in a vacuum oven with fresh 85% methymecrylate/15% dibutylphthalate/but now with 5% benzoyl peroxide for 48 hours (>20 vol per tissue vol). Following cooling to −20C for 30 minutes, the glass vial is carefully broken with a hammer and the plastic block containing distal femurs with implant manually trimmed with a band saw. Subsequent sectioning (50 micron) with a Leica SP1600 diamond saw microtome (cuts soft metals including titanium as well as bone), cutting sections longitudinal/parallel to the long axis of the implant onto chrom-alum gel coated slides. After deplastination in Cellsolve and rehydration through graded ethanol, bone tissue including osteoblasts and osteoids is visualized by 1% toluidine blue (pH=3.7), rinsed in citrate buffer, dehydrated in butanol/xylenes, and mounted (Permount) and cover slipped. Digital JPEG photomicrographs of the terminal implant bone interface (3 per specimen) are analyzed by ImageJ64/BoneJ plugin in lieu of osteomeasure[58, 77, 78] to characterize the distal 5%/0.1 mm of implant—encompassing approximately 2×0.1 mm+1 mm cylinder diameter=1.2 mm of implant surface—quantifying the bone-implant contact surface (percent BS/IS=bone surface to implant surface) and bone volume to tissue volume (BV/TV)[80] in the 250 micron segment abutting the distal end of the implant.

Example: Immunohistological assessment of NFkB activation and osteoclast numbers in bone adjacent to femoral implants in decalcified paraffin sections (n=5/group).: The distal ⅓ of the implant femur is harvested, carefully cleared of adherent tissue and fixed for 2 days in 10% neutral buffer formalin with shaking at 4C in 20 ml glass Wheaton vials. Subsequently, tissue is decalcified for 3 week using 0.375M EDTA pH8 at 4 with stirring[58]. Samples are then embedded in paraffin by the Pathology Core, and 5 micron paraffin sections cut orthogonal to the long axis of the implant, prepared from medial to lateral surface of the distal femur until the implant is encountered.

Luciferase reporter expression, nuclear NFkB accumulation, TRAP and TNAP (bone alkaline phosphatase[58, 81]) elaboration is assessed by immunohistochemistry in adjacent sections at 15-40 micron (Zone 1; roughly 1 osteoclast diameter), 70-90 micron (Zone 2), 140-160 micron (Zone 3), and 200-220 micron (Zone 4—approaching contralateral subperiosteum) penumbra distances from the distal end of the implant using the Vector ImmPress immunohistochemical dendrimer HRP enhanced method previously implemented[57, 58, 81] with light hematoxylin counterstaining. (Note: the 10 mM $H_2O_2$ used to quench endogenous peroxidase far exceeds the catalytic activity of nanoceria, and any background signal is identified with control sections lacking incubation with primary or secondary antibodies).

Digital photomicrographs are analyzed by ImageJ64/BoneJ plugin to characterize the expression area (% of tissue volume) of the luciferase NFkB reporter by immunohistochemistry, TRAP (osteoclast marker), TNAP (osteoblast marker), and nuclear NFkB2 (inflammatory NFkB activation marker) in the 4 zones abutting the inserted end of the titanium implants with or without nanoceria coatings.

Example: Assessment of Integration Using Push-In Uniaxial Load Testing of Titanium Implants with or without Nanoceria Coating Uniaxial "push in" loading following the method of Lanske[20, 70] is implemented to characterize osseous integration, a technique adopted from the dental literature. The push-in test has emerged as more sensitive that the pull-out test for mechanical assessment of the bone-implant interface in preclinical models[71]. Briefly, the entire right femur containing the distal implant will be harvested, carefully cleared of adherent tissue. The entire bone to the level of the implant site (side up) is placed in a rectangular cassette preloaded with self-polymerizing acrylic (Jet Denture Repair Acrylic), then anchored to the platen of an Intron 5944 universal microtester. The compression "needle" chuck (Instron Si-11862-1) is fitted with a 2 cm long×0.8 mm diameter stainless steel loading pin (Washington University School of Medicine Instrument Machine Shop; Dennis Tapella, Mgr), and uniaxial compression loading of the bone-integrated titanium prosthetic delivered 1 mm/minute along the long axis[20, 70], collecting force-displacement data with the Bluehill 3 Testing Software for Windows 7 and accompanying Biomedical Materials and Devices Module. Force-displacement curves will be analyzed characterizing, yield point, ultimate stress, and area under curve to characterize resistance of periprosthetic underlying bone to fracture[20, 70, 82]. Additionally, force-displacement curves to identify regions optimally characterizing the tissue modulus are analyzed.

The NC-coated titanium implants in the in vivo model may exhibit increased bone-implant contact surface, reduced NFkB activation and osteoclast formation (TRAP immunohistochemistry), improved osteoblast numbers/bone formation activity at the interface (TNAP immunohistochemistry), and increased adjacent bone volume to tissue volume (BVirV)[80] as compared with titanium implants alone. Push-in testing may reveal improved mechanical strength at the implant/bone interface in the presence of NC coating.

A dietary challenge is introduced in this procedure to induce the diabetic and dyslipidemia state in all LDLR−/− mice; this could represent too severe an impairment of bone healing[14] for nanoceria or NP's to overcome alone. In that event, the impact of coatings on intermittent PTH-induced bone formation—a strategy that has been shown to reduce oxidative stress in bone[84, 85] and vasculature 16 and recently demonstrated to enhance osseous integration in mice[86]—are examined using the general outline in FIG. 12.

The above description is provided as an aid in examining particular aspects of the invention, and represents only certain embodiments and explanations of embodiments. The examples are in no way meant to be limiting of the invention scope. The materials and methods provided below are those which were used in performing the examples that follow.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively.

Accordingly, all such modifications are intended to be included within the scope of this invention as defined in the following claims, in accordance with relevant law as to their interpretation.

REFERENCES

1. Murphy L B, Helmick C G, Allen K D, Theis K A, Baker N A, Murray G R, Qin J, Hootman J M, Brady T J, Barbour K E, Centers for Disease C, Prevention. Arthritis among veterans—united states, 2011-2013. *MMWR. Morbidity and mortality weekly report.* 2014; 63:999-1003
2. King K B, Findley T W, Williams A E, Bucknell A L. Veterans with diabetes receive arthroplasty more frequently and at a younger age. *Clinical orthopaedics and related research.* 2013; 471:3049-3054
3. Beck R T, Illingworth K D, Saleh K J. Review of periprosthetic osteolysis in total joint arthroplasty: An emphasis on host factors and future directions. *Journal of orthopaedic research: official publication of the Orthopaedic Research Society.* 2012; 30:541-546
4. Wukich D K. Diabetes and its negative impact on outcomes in orthopaedic surgery. *World J Orthop.* 2015; 6:331-339
5. Watts C D, Houdek M T, Wagner E R, Abdel M P, Taunton M J. Insulin dependence increases the risk of failure after total knee arthroplasty in morbidly obese patients. *The Journal of arthroplasty.* 2015
6. Rodriguez E K, Boulton C, Weaver M J, Herder L M, Morgan J H, Chacko A T, Appleton P T, Zurakowski D, Vrahas M S. Predictive factors of distal femoral fracture nonunion after lateral locked plating: A retrospective multicenter case-control study of 283 fractures. *Injury.* 2014; 45:554-559
7. Yang Z, Liu H, Xie X, Tan Z, Qin T, Kang P. The influence of diabetes mellitus on the post-operative outcome of elective primary total knee replacement: A systematic review and meta-analysis. *Bone Joint J.* 2014; 96-B:1637-1643
8. Kurtz S, Ong K, Lau E, Mowat F, Halpern M. Projections of primary and revision hip and knee arthroplasty in the united states from 2005 to 2030. *The Journal of bone and joint surgery. American volume.* 2007; 89:780-785
9. Purdue P E, Koulouvaris P, Nestor B J, Sculco T P. The central role of wear debris in periprosthetic osteolysis. *HSS journal: the musculoskeletal journal of Hospital for Special Surgery.* 2006; 2:102-113
10. Das S, Dowding J M, Klump K E, McGinnis J F, Self W, Seal S. Cerium oxide nanoparticles: Applications and prospects in nanomedicine. *Nanomedicine.* 2013; 8:1483-1508
11. Yang C, McCoy K, Davis J L, Schmidt-Supprian M, Sasaki Y, Faccio R, Novack D V. Nik stabilization in osteoclasts results in osteoporosis and enhanced inflammatory osteolysis. *PloS one.* 2010; 5:e15383
12. Vaira S, Johnson T, Hirbe A C, Alhawagri M, Anwisye I, Sammut B, O'Neal J, Zou W, Weilbaecher K N, Faccio R, Novack D V. Relb is the nf-kappab subunit downstream of nik responsible for osteoclast differentiation. *Proceedings of the National Academy of Sciences of the United States of America.* 2008; 105:3897-3902
13. Vaira S, Alhawagri M, Anwisye I, Kitaura H, Faccio R, Novack D V. Rela/p65 promotes osteoclast differentiation by blocking a rank1-induced apoptotic jnk pathway in mice. *The Journal of clinical investigation.* 2008; 118:2088-2097
14. Pirih F, Lu J, Ye F, Bezouglaia O, Atti E, Ascenzi M G, Tetradis S, Demer L, Aghaloo T, Tintut Y. Adverse effects of hyperlipidemia on bone regeneration and strength. *Journal of bone and mineral research: the official journal of the American Society for Bone and Mineral Research.* 2012; 27:309-318
15. Thompson B, Towler D A. Arterial calcification and bone physiology: Role of the bone-vascular axis. *Nat Rev Endocrinol.* 2012; 8:529-543
16. Cheng S L, Shao J S, Halstead L R, Distelhorst K, Sierra O, Towler D A. Activation of vascular smooth muscle parathyroid hormone receptor inhibits wnt/beta-catenin signaling and aortic fibrosis in diabetic arteriosclerosis. *Circulation research.* 2010; 107:271-282
17. Lai C F, Seshadri V, Huang K, Shao J S, Cai J, Vattikuti R, Schumacher A, Loewy A P, Denhardt D T, Rittling S R, Towler D A. An osteopontin-nadph oxidase signaling cascade promotes pro-matrix metalloproteinase 9 activation in aortic mesenchymal cells. *Circulation research.* 2006; 98:1479-1489
18. Towler D A, Bidder M, Latifi T, Coleman T, Semenkovich C F. Diet-induced diabetes activates an osteogenic gene regulatory program in the aortas of low density lipoprotein receptor-deficient mice. *The Journal of biological chemistry.* 1998; 273:30427-30434
19. Shao J S, Sierra O L, Cohen R, Mecham R P, Kovacs A, Wang J, Distelhorst K, Behrmann A, Halstead L R, Towler D A. Vascular calcification and aortic fibrosis: A bifunctional role for osteopontin in diabetic arteriosclerosis. *Arterioscler Thromb Vasc Biol.* 2011; 31:1821-1833
20. Sun N, Guo Y, Liu W, Densmore M, Shalhoub V, Erben R G, Ye L, Lanske B, Yuan Q. Fgf23 neutralization improves bone quality and osseointegration of titanium implants in chronic kidney disease mice. *Scientific reports.* 2015; 5:8304
21. Das S, Singh S, Dowding J M, Oommen S, Kumar A, Sayle T X, Saraf S, Patra C R, Vlahakis N E, Sayle D C, Self W T, Seal S. The induction of angiogenesis by cerium oxide nanoparticles through the modulation of oxygen in intracellular environments. *Biomaterials.* 2012; 33:7746-7755
22. Dickinson B C, Huynh C, Chang C J. A palette of fluorescent probes with varying emission colors for imaging hydrogen peroxide signaling in living cells. *Journal of the American Chemical Society.* 2010; 132:5906-5915
23. McCormack R N, Mendez P, Barkam S, Neal C J, Das S, Seal S. Inhibition of nanoceria's catalytic activity due to ce3+ site-specific interaction with phosphate ions. *The Journal of Physical Chemistry C* 2013; 118:18992-19006.
24. Naganuma T, Traversa E. The effect of cerium valence states at cerium oxide nanoparticle surfaces on cell proliferation. *Biomaterials.* 2014; 35:4441-4453
25. Grosse S, Haugland H K, Lilleng P, Ellison P, Hallan G, Hol P J. Wear particles and ions from cemented and uncemented titanium-based hip prostheses-a histological and chemical analysis of retrieval material. Journal of biomedical materials research. Part B, *Applied biomaterials.* 2015; 103:709-717

26. Gupta A, Tripathi G, Lahiri D, Balani K. Compression molded ultra high molecular weight polyethylene-hydroxyapatite-aluminum oxide-carbon nanotube hybrid composites for hard tissue replacement. *Journal of Materials Science & Technology* 2013; 29:514-522.

27. Baier R E. Surface behaviour of biomaterials: The theta surface for biocompatibility. *J Mater Sci Mater Med.* 2006; 17:1057-1062

28. Chigurupati S, Mughal M R, Okun E, Das S, Kumar A, McCaffery M, Seal S, Mattson M P. Effects of cerium oxide nanoparticles on the growth of keratinocytes, fibroblasts and vascular endothelial cells in cutaneous wound healing. *Biomaterials.* 2013; 34:2194-2201

29. Biswas R, Sanders R. The effects of a ceo2 coating on the corrosion parameters of type 304 stainless steel. *Journal of materials engineering and performance.* 1998; 7:727-732

30. Yang Y, Han J, Ning X, Cao W, Xu W, Guo L. Controllable morphology and conductivity of electrodeposited cu(2)o thin film: Effect of surfactants. *ACS Appl Mater Interfaces.* 2014; 6:22534-22543

31. Montemor M F, Pinto R, Ferreira M. Chemical composition and corrosion protection of silane films modified with ceo 2 nanoparticles. *Electrochimica Acta* 2009; 54:5179-5189.

32. Hamdy A S. Advanced nano-particles anti-corrosion ceria based sol gel coatings for aluminum alloys. *Materials Letters.* 2006; 60:2633-2637

33. Ishizaki T, Masuda Y, Sakamoto M. Corrosion resistance and durability of superhydrophobic surface formed on magnesium alloy coated with nanostructured cerium oxide film and fluoroalkylsilane molecules in corrosive nacl aqueous solution. *Langmuir: the ACS journal of surfaces and colloids.* 2011; 27:4780-4788

34. Wang Y, Wei M, Gao J, Hu J, Zheng Y. Corrosion process of pure magnesium in simulated body fluid. *Materials letters.* 2008; 62: 2181-2184

35. Huang C H, Lai J J, Wei T Y, Chen Y H, Wang X, Kuan S Y, Huang J C. Improvement of bio-corrosion resistance for ti42zr40si15ta3 metallic glasses in simulated body fluid by annealing within supercooled liquid region. *Mater Sci Eng C Mater Biol Appl.* 2015; 52:144-150

36. Kim W-H, Kim M-K, Maeng W, Gatineau J, Pallem V, Dussarrat C, Noorin A, Thompson D D, Chu S, Kim H. Growth characteristics and film properties of cerium dioxide prepared by plasma-enhanced atomic layer deposition. *Journal of The Electrochemical Society* 2011; 158:G169-G172

37. Korsvik C, Patil S, Seal S, Self W T. Superoxide dismutase mimetic properties exhibited by vacancy engineered ceria nanoparticles. *Chemical communications.* 2007:1056-1058

38. Heckert E G, Karakoti A S, Seal S, Self W T. The role of cerium redox state in the sod mimetic activity of nanoceria. *Biomaterials.* 2008; 29:2705-2709

39. Pirmohamed T, Dowding J M, Singh S, Wasserman B, Heckert E, Karakoti A S, King J E, Seal S, Self W T. Nanoceria exhibit redox state-dependent catalase mimetic activity. *Chemical communications.* 2010; 46:2736-2738

40. Dowding J M, Dosani T, Kumar A, Seal S, Self W T. Cerium oxide nanoparticles scavenge nitric oxide radical (no). *Chemical communications.* 2012; 48:4896-4898

41. Dowding J M, Das S, Kumar A, Dosani T, McCormack R, Gupta A, Sayle T X, Sayle D C, von Kalm L, Seal S, Self W T. Cellular interaction and toxicity depend on physicochemical properties and surface modification of redox-active nanomaterials. *ACS nano.* 2013; 7:4855-4868

42. Walkey C, Das S, Seal S, Erlichman J, Heckman K, Ghibelli L, Traversa E, McGinnis J F, Self W T. Catalytic properties and biomedical applications of cerium oxide nanoparticles. *Environ Sci Nano.* 2015; 2:33-53

43. Cai X, Seal S, McGinnis J F. Sustained inhibition of neovascularization in vldlr-/- mice following intravitreal injection of cerium oxide nanoparticles and the role of the ask1-p38/jnk-nf-kappab pathway. *Biomaterials.* 2014; 35:249-258

44. Cai X, Yodoi J, Seal S, McGinnis J F. Nanoceria and thioredoxin regulate a common antioxidative gene network in tubby mice. *Advances in experimental medicine and biology.* 2014; 801:829-836

45. Heckman K L, DeCoteau W, Estevez A, Reed K J, Costanzo W, Sanford D, Leiter J C, Clauss J, Knapp K, Gomez C, Mullen P, Rathbun E, Prime K, Marini J, Patchefsky J, Patchefsky A S, Hailstone R K, Erlichman J S. Custom cerium oxide nanoparticles protect against a free radical mediated autoimmune degenerative disease in the brain. *ACS nano.* 2013; 7:10582-10596

46. Hirst S M, Karakoti A, Singh S, Self W, Tyler R, Seal S, Reilly C M. Bio-distribution and in vivo antioxidant effects of cerium oxide nanoparticles in mice. *Environmental toxicology.* 2013; 28:107-118

47. Hirst S M, Karakoti A S, Tyler R D, Sriranganathan N, Seal S, Reilly C M. Anti-inflammatory properties of cerium oxide nanoparticles. *Small.* 2009; 5:2848-2856

48. Lung S, Cassee F R, Gosens I, Campbell A. Brain suppression of ap-1 by inhaled diesel exhaust and reversal by cerium oxide nanoparticles. *Inhal Toxicol.* 2014; 26:636-641

49. Rocca A, Moscato S, Ronca F, Nitti S, Mattoli V, Giorgi M, Ciofani G. Pilot in vivo investigation of cerium oxide nanoparticles as a novel anti-obesity pharmaceutical formulation. *Nanomedicine: nanotechnology, biology, and medicine.* 2015; 11:1725-1734

50. Dowding J M, Song W, Bossy K, Karakoti A, Kumar A, Kim A, Bossy B, Seal S, Ellisman M H, Perkins G, Self W T, Bossy-Wetzel E. Cerium oxide nanoparticles protect against abeta-induced mitochondrial fragmentation and neuronal cell death. *Cell death and diferentiation.* 2014; 21:1622-1632

51. Abu-Amer Y, Darwech I, Clohisy J C. Aseptic loosening of total joint replacements: Mechanisms underlying osteolysis and potential therapies. *Arthritis research & therapy.* 2007; 9 Suppl 1:S6

52. Cronin J G, Turner M L, Goetze L, Bryant C E, Sheldon I M. Toll-like receptor 4 and myd88-dependent signaling mechanisms of the innate immune system are essential for the response to lipopolysaccharide by epithelial and stromal cells of the bovine endometrium. *Biol Reprod.* 2012; 86:51

53. Kruger B, Yin N, Zhang N, Yadav A, Coward W, Lal G, Zang W, P S H, Bromberg J S, Murphy B, Schroppel B. Islet-expressed thr2 and tlr4 sense injury and mediate early graft failure after transplantation. *European journal of immunology.* 2010; 40:2914-2924

54. Soloviev A, Schwarz E M, Kuprash D V, Nedospasov S A, Puzas J E, Rosier R N, O'Keefe R J. The role of p105 protein in nfkappab activation in ana-1 murine macrophages following stimulation with titanium particles.

*Journal of orthopaedic research: official publication of the Orthopaedic Research Society.* 2002; 20:714-722

55. Platt I D, Josse A R, Kendall C W, Jenkins D J, El-Sohemy A. Postprandial effects of almond consumption on human osteoclast precursors—an ex vivo study. *Metabolism.* 2011; 60:923-929

56. Katagiri M, Hakeda Y, Chikazu D, Ogasawara T, Takato T, Kumegawa M, Nakamura K, Kawaguchi H. Mechanism of stimulation of osteoclastic bone resorption through gas6/tyro 3, a receptor tyrosine kinase signaling, in mouse osteoclasts. *The Journal of biological chemistry.* 2001; 276:7376-7382

57. Cheng S L, Ramachandran B, Behrmann A, Shao J S, Mead M, Smith C, Krchma K, Bello Arredondo Y, Kovacs A, Kapoor K, Brill L M, Perera R, Williams B O, Towler D A. Vascular smooth muscle lrp6 limits arteriosclerotic calcification in diabetic ldlr−/− mice by restraining non-canonical wnt signals. *Circulation research.* 2015; 117:142-156

58. Cheng S L, Shao J S, Cai J, Sierra O L, Towler D A. Msx2 exerts bone anabolism via canonical wnt signaling. *The Journal of biological chemistry.* 2008; 283:20505-20522

59. Shao J S, Cheng S L, Charlton-Kachigian N, Loewy A P, Towler D A. Teriparatide (human parathyroid hormone (1-34)) inhibits osteogenic vascular calcification in diabetic low density lipoprotein receptor-deficient mice. The Journal of biological chemistry. 2003; 278:50195-50202

60. Hirakawa K, Bauer T W, Stulberg B N, Wilde A H. Comparison and quantitation of wear debris of failed total hip and total knee arthroplasty. *J Biomed Mater Res.* 1996; 31:257-263

61. Ponnusamy M, Liu N, Sellamuthu R, Zhao T C, Mao H, Zhuang S. Autophagy protects against necrotic renal epithelial cell-induced death of renal interstitial fibroblasts. *American journal of physiology. Renal physiology.* 2012; 303:F83-91

62. Keegan G M, Learmonth I D, Case C P. Orthopaedic metals and their potential toxicity in the arthroplasty patient: A review of current knowledge and future strategies. The *Journal of bone and joint surgery. British volume.* 2007; 89:567-573

63. Yadav V R, Prasad S, Sung B, Aggarwal B B. The role of chalcones in suppression of nf-kappab-mediated inflammation and cancer. *Int Immunopharmacol.* 2011; 11:295-309

64. Noor Z, Kania N, Setiawan B. Tibia bone properties at different time course of ovariectomized rats. *J Diabetes Metab Disord.* 2014; 13:91

65. Faienza M F, Ventura A, Piacente L, Ciccarelli M, Gigante M, Gesualdo L, Colucci S, Cavallo L, Grano M, Brunetti G. Osteoclastogenic potential of peripheral blood mononuclear cells in cleidocranial dysplasia. *Int J Med Sci.* 2014; 11:356-364

66. Lai C F, Shao J S, Behrmann A, Krchma K, Cheng S L, Towler D A. Tnfr1-activated reactive oxidative species signals up-regulate osteogenic msx2 programs in aortic myofibroblasts. *Endocrinology.* 2012; 153:3897-3910

67. Cheng S L, Shao J S, Behrmann A, Krchma K, Towler D A. Dkk1 and msx2-wnt7b signaling reciprocally regulate the endothelial-mesenchymal transition in aortic endothelial cells. *Arterioscler Thromb Vasc Biol.* 2013; 33:1679-1689

68. Olivares-Navarrete R, Raines A L, Hyzy S L, Park J H, Hutton D L, Cochran D L, Boyan B D, Schwartz Z. Osteoblast maturation and new bone formation in response to titanium implant surface features are reduced with age. Journal of bone and mineral research: the official journal of the American Society for Bone and Mineral Research. 2012; 27:1773-1783

69. Kayal R A, Tsatsas D, Bauer M A, Allen B, Al-Sebaei M O, Kakar S, Leone C W, Morgan E F, Gerstenfeld L C, Einhorn T A, Graves D T. Diminished bone formation during diabetic fracture healing is related to the premature resorption of cartilage associated with increased osteoclast activity. *Journal of bone and mineral research: the official journal of the American Society for Bone and Mineral Research.* 2007; 22:560-568

70. Zou H, Zhao X, Sun N, Zhang S, Sato T, Yu H, Chen Q, Weber H P, Dard M, Yuan Q, Lanske B. Effect of chronic kidney disease on the healing of titanium implants. *Bone.* 2013; 56:410-415

71. Seong W J, Grami S, Jeong S C, Conrad H J, Hodges J S. Comparison of push-in versus pull-out tests on bone-implant interfaces of rabbit tibia dental implant healing model. *Clin Implant Dent Relat Res.* 2013; 15:460-469

72. Kilkenny C, Browne W J, Cuthill I C, Emerson M, Altman D G. Improving bioscience research reporting: The arrive guidelines for reporting animal research. *Osteoarthritis and cartilage/OARS, Osteoarthritis Research Society.* 2012; 20:256-260

73. Bolli R. The new circulation research: A manifesto. *Circulation research.* 2010; 106:216-226

74. Windahl S H, Lagerquist M K, Andersson N, Jochems C, Kallkopf A, Hakansson C, Inzunza J, Gustafsson J A, van der Saag P T, Carlsten H, Pettersson K, Ohlsson C. Identification of target cells for the genomic effects of estrogens in bone. *Endocrinology.* 2007; 148:5688-5695

75. Cheng S L, Behrmann A, Shao J S, Ramachandran B, Krchma K, Bello Arredondo Y, Kovacs A, Mead M, Maxson R, Towler D A. Targeted reduction of vascular msx1 and msx2 mitigates arteriosclerotic calcification and aortic stiffness in ldlr-deficient mice fed diabetogenic diets. *Diabetes.* 2014; 63:4326-4337

76. Wohl G R, Towler D A, Silva M J. Stress fracture healing: Fatigue loading of the rat ulna induces upregulation in expression of osteogenic and angiogenic genes that mimic the intramembranous portion of fracture repair. *Bone.* 2009; 44:320-330

77. Schmidt A, Harada S, Kimmel D B, Bai C, Chen F, Rutledge S J, Vogel R L, Scafonas A, Gentile M A, Nantermet P V, McElwee-Witmer S, Pennypacker B, Masarachia P, Sahoo S P, Kim Y, Meissner R S, Hartman G D, Duggan M E, Rodan G A, Towler D A, Ray W J. Identification of anabolic selective androgen receptor modulators with reduced activities in reproductive tissues and sebaceous glands. *The Journal of biologicalchemistry.* 2009; 284:36367-36376

78. Scafonas A, Reszka A A, Kimmel D B, Hou X S, Su Q, Birzin E T, Kim S, Chen H Y, Tan Q, Roher S P, Dininno F, Hammond M L, Rodan G A, Towler D A, Schmidt A. Agonist-like serm effects on eralpha-mediated repression of mmp1 promoter activity predict in vivo effects on bone and uterus. *J Steroid Biochem Mol Biol.* 2008; 110:197-206

79. Troiano N W, Ciovacco W A, Kacena M A. The effects of fixation and dehydration on the histological quality of undecalcified murine bone specimens embedded in methylmethacrylate. *J Histotechnol.* 2009; 32:27-31

80. Dempster D W, Compston J E, Drezner M K, Glorieux F H, Kanis J A, Malluche H, Meunier P J, Ott S M, Recker R R, Parfitt A M. Standardized nomenclature, symbols, and units for bone histomorphometry: A 2012 update of the report of the asbmr histomorphometry nomenclature committee. *Journal of bone and mineral research: the official journal of the American Society for Bone and Mineral Research.* 2013; 28:2-17

81. Shao J S, Cheng S L, Pingsterhaus J M, Charlton-Kachigian N, Loewy A P, Towler D A. Msx2 promotes cardiovascular calcification by activating paracrine wnt signals. *The Journal of clinical investigation.* 2005; 115: 1210-1220

82. Silva M J. Biomechanics of osteoporotic fractures. *Injury.* 2007; 38 Suppl 3:S69-76

83. Jepsen K J, Silva M J, Vashishth D, Guo X E, van der Meulen M C. Establishing biomechanical mechanisms in mouse models: Practical guidelines for systematically evaluating phenotypic changes in the diaphyses of long bones. *Journal of bone and mineral research: the official journal of the American Society for Bone and Mineral Research.* 2015; 30:951-966

84. Jilka R L, Almeida M, Ambrogini E, Han L, Roberson P K, Weinstein R S, Manolagas S C. Decreased oxidative stress and greater bone anabolism in the aged, when compared to the young, murine skeleton with parathyroid hormone administration. *Aging cell.* 2010; 9:851-867

85. Almeida M, Ambrogini E, Han L, Manolagas S C, Jilka R L. Increased lipid oxidation causes oxidative stress, increased peroxisome proliferator-activated receptor-gamma expression, and diminished pro-osteogenic wnt signaling in the skeleton. *The Journal of biological chemistry.* 2009; 284:27438-27448

86. Yang X, Ricciardi B F, Dvorzhinskiy A, Brial C, Lane Z, Bhimani S, Burket J C, Hu B, Sarkisian A M, Ross F P, van der Meulen M C, Bostrom M P. Intermittent parathyroid hormone enhances cancellous osseointegration of a novel murine tibial implant. *The Journal of bone and joint surgery. American volume.* 2015; 97:1074-1083

87. Nyazee H A, Finney K M, Sarikonda M, Towler D A, Johnson J E, Babcock H M. Diabetic foot osteomyelitis: Bone markers and treatment outcomes. *Diabetes Res Clin Pract.* 2012; 97:411-417

88. Novack D V, Teitelbaum S L. The osteoclast: friend or foe? Annu Rev pathmechdis Mech Dis. 2008; 3:457-84.

What is claimed is:

1. A method for forming a coating comprising steps of:
providing a substrate; and
electrophoretically forming the coating on at least a portion of the substrate using a dispersion;
wherein the dispersion comprises ceria nanoparticles with cerium predominantly in a $Ce^{3+}$ oxidation state on the surface thereof (NC1) or the ceria nanoparticles with cerium predominantly in a higher $Ce^{4+}$ oxidation state on the surface thereof (NC2), or a mixture of NC1 and NC2;
wherein NC1 and NC2 comprise the ceria nanoparticles having a size in a range of 3-5 nm; and
wherein the coating exhibits catalase mimetic activity, superoxide dismutase mimetic activity, or both.

2. The method of claim 1, wherein the electrophoretic forming step is carried out by applying a voltage having a DC component and/or an AC component to the substrate and at least one counter-electrode, wherein the voltage is continuous, pulsed, or arbitrarily increasing or decreasing with time.

3. The method of claim 2, wherein the at least one counter-electrode comprises two counter-electrodes.

4. The method of claim 1, further comprising after the coating has been formed, heating the substrate to 200-450° C. for 1-2.5 hr.

5. The method as recited in claim 1, wherein one electrode is a Ti electrode and two electrodes are nonconsumable counter-electrodes.

6. The method of claim 1, wherein the substrate comprises a prosthesis.

* * * * *